United States Patent
Buckland et al.

(10) Patent No.: US 10,048,057 B2
(45) Date of Patent: *Aug. 14, 2018

(54) IMAGE REGISTRATION, AVERAGING, AND COMPOUNDING FOR HIGH SPEED EXTENDED DEPTH OPTICAL COHERENCE TOMOGRAPHY

(71) Applicant: Bioptigen, Inc., Morrisville, NC (US)

(72) Inventors: Eric L. Buckland, Hickory, NC (US); Al-Hafeez Z. Dhalla, Durham, NC (US); Nestor O. Farmiga, Rochester, NY (US); Mehran Ghofrani, Cary, NC (US); Robert H. Hart, Cary, NC (US); Andrew Murnan, Saratoga Springs, NY (US); Christopher Saxer, Cary, NC (US)

(73) Assignee: Bioptigen, Inc., Morrisville, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/190,299

(22) Filed: Jun. 23, 2016

(65) Prior Publication Data
US 2016/0298953 A1    Oct. 13, 2016

Related U.S. Application Data

(63) Continuation of application No. 14/561,772, filed on Dec. 5, 2014, now Pat. No. 9,377,291.
(Continued)

(51) Int. Cl.
*G01B 9/02* (2006.01)
*A61B 3/10* (2006.01)

(52) U.S. Cl.
CPC .......... *G01B 9/02087* (2013.01); *A61B 3/102* (2013.01); *G01B 9/02004* (2013.01);
(Continued)

(58) Field of Classification Search
None
See application file for complete search history.

(56) References Cited

U.S. PATENT DOCUMENTS

| 4,580,219 A | 4/1986 | Pelc et al. |
| 5,150,421 A | 9/1992 | Morishita et al. |

(Continued)

FOREIGN PATENT DOCUMENTS

WO    WO2004/002298 A1    1/2004

OTHER PUBLICATIONS

Dainty, J.C. (ed.), "Laser Speckle and Related Phenomena," Springer-Verlag, New York (1984).
(Continued)

*Primary Examiner* — Shawn Decenzo
(74) *Attorney, Agent, or Firm* — Ward and Smith, P.A.

(57) ABSTRACT

An optical coherence tomography (OCT) system including a source of broadband optical radiation and a beamsplitter coupled to the source is provided. The beamsplitter divides the source radiation into a reference path and a sample path. The reference path includes an optical switch to switch the reference path between a first path having a first reference reflection at a first reference optical path length and a second path having a second reference reflection at a second reference optical path length. The system further includes a beam combiner that mixes source radiation reflected from a subject in the sample path with source radiation returned from the first reference reflection and the second reference reflection. A detection system detects a first wavelength dependent interferogram during the first time interval and a second wavelength dependent interferogram during the second time interval. A processor preconditions the first and second wavelength dependent interferograms.

20 Claims, 16 Drawing Sheets

Related U.S. Application Data

(60) Provisional application No. 61/912,160, filed on Dec. 5, 2013.

(52) U.S. Cl.
CPC ..... *G01B 9/02028* (2013.01); *G01B 9/02044* (2013.01); *G01B 9/02091* (2013.01)

(56) References Cited

U.S. PATENT DOCUMENTS

| | | | |
|---|---|---|---|
| 5,204,627 | A | 4/1993 | Mistretta et al. |
| 5,226,113 | A | 7/1993 | Cline et al. |
| 5,233,299 | A | 8/1993 | Souza et al. |
| 5,297,551 | A | 3/1994 | Margosian et al. |
| 5,368,033 | A | 11/1994 | Moshfeghi |
| 5,760,781 | A | 6/1998 | Kaufman et al. |
| 5,852,646 | A | 12/1998 | Klotz et al. |
| 6,102,864 | A | 8/2000 | Hatfield et al. |
| 6,112,112 | A | 8/2000 | Gilhuijs et al. |
| 6,436,049 | B1 | 8/2002 | Kamiyama et al. |
| 6,459,094 | B1 | 10/2002 | Wang et al. |
| 6,490,335 | B1 | 12/2002 | Wang et al. |
| 6,519,354 | B1 | 2/2003 | Oshio |
| 6,671,538 | B1 | 12/2003 | Ehnholm et al. |
| 6,885,764 | B2 | 4/2005 | Wang et al. |
| 6,904,163 | B1 | 6/2005 | Fujimura et al. |
| 6,907,281 | B2 | 6/2005 | Grzeszczuk |
| 7,020,318 | B2 | 3/2006 | Oshio et al. |
| 7,170,517 | B2 | 1/2007 | Raman et al. |
| 7,301,644 | B2 | 11/2007 | Knighton et al. |
| 7,505,142 | B2 | 3/2009 | Knighton et al. |
| 7,532,750 | B2 | 5/2009 | Sasaki et al. |
| 7,623,736 | B2 | 11/2009 | Viswanathan |
| 8,425,037 | B2 | 4/2013 | Uhlhorn ................. A61B 3/102 351/206 |
| 9,076,202 | B2 | 7/2015 | Courtney ............ A61B 5/0066 |
| 2001/0036303 | A1 | 11/2001 | Maurincomme et al. |
| 2003/0088542 | A1 | 5/2003 | McGee et al. |
| 2004/0215071 | A1 | 10/2004 | Frank et al. |
| 2004/0239938 | A1 | 12/2004 | Izatt |
| 2005/0018201 | A1 | 1/2005 | de Boer et al. |
| 2005/0049478 | A1 | 3/2005 | Kuduvalli et al. |
| 2005/0065421 | A1 | 3/2005 | Burckhardt |
| 2005/0105828 | A1 | 5/2005 | Oosawa |
| 2005/0111720 | A1 | 5/2005 | Gurcan et al. |
| 2005/0140984 | A1 | 6/2005 | Hitzenberger |
| 2005/0226375 | A1 | 10/2005 | Eberhard et al. |
| 2006/0030768 | A1 | 2/2006 | Ramamurthy et al. |
| 2007/0002327 | A1 | 1/2007 | Zhou et al. |
| 2007/0003117 | A1 | 1/2007 | Wheeler et al. |
| 2007/0066880 | A1 | 3/2007 | Lee et al. |
| 2007/0291277 | A1 | 12/2007 | Everett et al. |
| 2008/0002062 | A1 | 1/2008 | Kim et al. |
| 2008/0095433 | A1 | 4/2008 | Johnson et al. |
| 2008/0187095 | A1 | 8/2008 | Boone et al. |
| 2010/0027857 | A1 | 2/2010 | Wang |
| 2015/0374228 | A1 | 12/2015 | Satake ................... A61B 3/102 351/206 |

OTHER PUBLICATIONS

Ruggeri et al., "Imaging and full-length biometry of the eye during accommodation using spectral domain OCT with an optical switch," Biomed. Opt. Exp. 3(7), 1506-1520 (2012).

Schmitt et al., "Speckle in Optical Coherence Tomography: An Overview," J. Biomed. Opt. 4, 95-105 (1999).

Wang et al., "Extending the effective imaging range of Fourier domain optical coherence tomography using a fiber optic switch," Opt. Lett. 32(22), 2632-2634 (2008).

Bruckner, Stefan, "Introduction to Scientific Visualization," Simon Fraser University/Vienna University of Technology, Applicants' Admitted Prior Art, 17 pages.

Choma et al., "Sensitivity advantage of swept source and Fourier domain optical coherence tomography," Optics Express, vol. 11, No. 18, Sep. 8, 2003, 2183-2189.

Dorrer et al., "Spectral resolution and sampling issues in Fourier-transformation spectral interferometry," J. Opt. Soc. Am. B, vol. 17, No. 10, Oct. 2000, 1795-1802.

Ferguson et al., "Tracking Optical Coherence Tomography," Optics Letters 29(18), pp. 2139-2141, Sep. 15, 2004.

First Office Action, Chinese Patent Application No. 200680036611.5, dated Aug. 20, 2010, 27 pages.

Häusler et al., "'Coherence Radar' and 'Spectral Radar'—New Tools for Dermatological Diagnosis," Journal of Biomedical Optics, vol. 3, No. 1, Jan. 1998, 21-31.

Heidrich et al., "Interactive Maximum Projection Volume Rendering," Sixth IEEE Visualization 1995 (VIS '95), Oct. 29-Nov. 3, 1995, 1 page.

Hylton, Nola M., "Angiographic display method for flow-enhanced MRI", Abstract, Publication Date Jun. 1992, http://adsabs.harvard.edu/abs/1992SPIE.1652.107H, 2 pages.

International Search Report and Written Opinion for PCT/US2006/029535; dated Aug. 22, 2007.

Jiao et al., "Simultaneous acquisition of sectional and fundus ophthalmic images with spectral-domain optical coherence tomography," Optics Express, Vo. 13, No. 2, Jan. 24, 2005, 444-452.

Jiao et al., "Registration of high-density cross sectional images to the fundus image in spectral-domain ophthalmic optical coherence tomography" *Optics Express*, vol. 14, No. 8, Apr. 17, 2006, 3368-3376.

Kaufman et al., "Real-Time Volume Rendering," to appear in the International Journal of Imaging Systems and Technology, special issue on 3D Imaging, Center for Visual Computing (CVC) and Department of Computer Science, State University of New York at Stony Brook, Applicants' Admitted Prior Art, 9 pages.

Leitgeb et al., "Performance of fourier domain vs. time domain optical coherence tomography," Optics Express, vol. 11, No. 8, Apr. 21, 2003, 889-894.

Mahmoud et al. "Comparison of three methods for registration of abdominal/pelvic volume data sets from functional-anatomic scans" Proc. of SPIE, vol. 3979, 1378-1386 (2000).

Office Action, Japanese Patent Application No. 2008-525059, dated May 8, 2012.

Srinivasan et al. "Three-dimensional retinal imaging with ultrahigh resolution, Fourier/spectral domain optical coherence tomography" Proc. of SPIE 5688(1):90-99 (2005).

Tan-no et al., "Optical multimode frequency-domain reflectometer," Optics Letters, vol. 19, No. 8, Apr. 15, 1994, 587-589.

Totsuka et al., "Frequency Domain Volume Rendering," Sony Corporation, Applicants' Admitted Prior Art, pp. 271-278.

Yun et al., "High-speed spectral-domain optical coherence tomography at 1.3 µm wavelength," Optics Express, vol. 11, No. 26, Dec. 29, 2003, 3598-3604.

IMAGE REGISTRATION, AVERAGING, AND COMPOUNDING FOR HIGH SPEED EXTENDED DEPTH OPTICAL COHERENCE TOMOGRAPHY

CLAIM OF PRIORITY

The present application is a continuation of U.S. patent application Ser. No. 14/561,772, filed Dec. 5, 2014 (now U.S. Pat. No. 9,377,291), which claims priority from U.S. Provisional Application No. 61/912,160, filed Dec. 5, 2013, the disclosures of which are hereby incorporated herein by reference as if set forth in their entirety.

FIELD

The present inventive concept relates generally to optical coherence tomography (OCT) systems and, more particularly, to methods of extending a useful depth range of Fourier domain OCT (FDOCT) with reference switching and real-time image registration and image blending.

BACKGROUND

Optical coherence tomography (OCT) is a non-contact, optical imaging modality that provides high-resolution cross-sectional images of the various layers of the anterior and posterior eye. In recent years, OCT has become the standard of care for diagnosing and monitoring therapy for many ophthalmic diseases, including age-related macular degeneration and diabetic retinopathy. OCT is also commonly used to aid in ophthalmic surgical planning and post-operative assessment, and more recently, has been used perioperatively via handheld probes mounted to the surgical microscope. Intrasurgical OCT systems integrated directly into the optical train of the surgical microscope are rapidly making their way to the clinic.

Each year, over 20 million ophthalmic surgeries are performed worldwide. Indications for ophthalmic surgery include potentially blinding diseases, such as cataracts, diabetic retinopathy, macular disease, and retinal detachment. Surgeons performing these delicate procedures are challenged by the translucent nature of tissues in the eye, making it nearly impossible to visualize microstructural changes during surgery. The high-resolution cross-sectional information provided by OCT is a natural complement to the microsurgical environment of an ophthalmic operating room. Intrasurgical OCT offers the surgeon the ability to see the microstructure of the eye in a way not possible with conventional surgical microscopes. By improving tissue visualization and providing surgical feedback, intraoperative OCT will enhance surgical precision, decrease surgical trauma, aid in surgical decision-making and ultimately improve functional and anatomical outcomes.

Preliminary research supports the utility of intrasurgical OCT and suggests that it may yield critical information regarding disease processes and the impact of surgical maneuvers, and thus aid surgical decision-making. Several surgical ophthalmic conditions have already been examined using intraoperative and perioperative imaging, including optic pit-related maculopathy, epiretinal membranes (ERM), macular holes, retinal detachments, and cataract surgery. Preliminary research has also shown that intrasurgical OCT can allow the surgeon to visualize the ultrastructural impact of a surgical maneuver on the tissue of interest. Documented changes in retinal architecture following ERM removal reveal alterations in retinal contour and, in some cases, microneurosensory retinal detachments. Intraoperative OCT during macular hole surgery has demonstrated changes in hole configuration following removal of the internal limiting membrane (ILM). Additionally, subclinical residual membranes have been identified that can be addressed during surgery. Finally, during intraocular lens (IOL) implantation, intraoperative OCT can be used to identify residual lens epithelial cells (LECs) in the posterior capsule, and also to evaluate adhesion of the posterior lens capsule to the IOL. Complete removal of residual LECs and good capsule-IOL adhesion are correlated with lower incidence of posterior capsule opacification, which occurs in as many as 30% of patients following cataract extraction.

Imaging of the ocular field in surgery benefits from a large depth of field in order to see the total physical extent of patho-physiology and trauma, to allow visualization of surgical instruments within the surgical field, and to allow the for the image OCT image to remain in view as the patient is subject to the various surgical manipulations that cause motion of the physical structure of the eye. Furthermore, the medium of the eye may become cloudy as the vitreous is stirred. For anterior imaging of the cornea and crystalline lens it is of specific interest to acquire deep images in order to visualize the entire affected optical structure during cornea and cataract surgeries. Surgical procedures require image depth and signal to noise improvement beyond the requirements of standard clinical diagnostic imaging.

In an article by Ruggeri et al entitled *Imaging and full-length biometry of the eye during accommodation using spectral domain OCT with an optical switch*, a reference arm switching technique is proposed to improve image depth in Fourier domain OCT (FDOCT), taking advantage of the nature of the Fourier domain signal processing. The signal to noise ratio (SNR) of Fourier domain images increases with distance from the path-matched, or direct current (DC) position of the image. Acquiring one image with the reference position on the proximal side of subject region and summing with a second image acquired with the reference position on the distal side of a subject region achieves the dual objectives of averaging to improve SNR generally, and balancing the SNR across the range of the image.

In order to be practically deployed, systems with reference arm switching function must operate in real-time, with image acquisition, image-pair rotation, registration, stitching, and display occurring with minimum latency. These tasks require both rapid switching and fast and accurate registration algorithms.

SUMMARY

Some embodiments of the present inventive concept provide an optical coherence tomography (OCT) system including a source of broadband optical radiation and a beamsplitter coupled to the source. The beamsplitter divides the source radiation into a reference path and a sample path. The reference path includes an optical switch to switch the reference path between a first path having a first reference reflection at a first reference optical path length and a second path having a second reference reflection at a second reference optical path length, different from the first reference optical path length. The system further includes a beam combiner that mixes source radiation reflected from a subject in the sample path with source radiation returned from the first reference reflection during a first time interval and the second reference reflection during a second time interval. A detection system detects a first wavelength dependent interferogram during the first time interval and a second wavelength dependent interferogram during the second time interval. A processor preconditions the first and second wavelength dependent interferograms; multiples the first preconditioned wavelength dependent interferogram and the second preconditioned wavelength dependent interferogram; and computes a first A-scan from the first wavelength dependent interferogram; a second A-scan from the second wavelength dependent interferogram; a spatial offset between the first and second A-scans derived from the multiplicative product of the preconditioned first and second wavelength dependent interferograms; and a combined A-scan from the first and second A-scans.

In further embodiments, the processor may be further configured to precondition the first and second spectral interferograms using one or more of wavelength to wavenumber resampling; background and/or reference subtraction; and addition of a wavelength dependent phase function.

In still further embodiments, the processor may be further configured to compute the combined A-scan using addition of the first and second A-scans; a depth-dependent blending of the first and second A-scans and/or an adaptive combination of the first and second A-scans.

In some embodiments, the OCT system may be a Fourier domain OCT (FDOCT) system, for example, a spectral domain OCT (SDOCT) system or a swept source OCT (SSOCT) system.

In further embodiments, the detection system may include a spectrometer.

In still further embodiments, the broadband source of optical radiation may radiate a time varying optical spectrum.

Some embodiments of the present inventive concept provide an optical coherence tomography (OCT) system including a source of broadband optical radiation and a beamsplitter coupled to the source. The beamsplitter divides the source radiation into a reference path and a sample path. The reference path includes an optical switch to switch the reference path between a first path having a first reference reflection at a first reference optical path length and a second path having a second reference reflection at a second reference optical path length, different from the first reference optical path length. A beam combiner mixes source radiation reflected from a subject in the sample path with source radiation returned from the first reference reflection during a first time interval and the second reference reflection during a second time interval. A detection system detects a first set of wavelength dependent interferograms during the first time interval and a second set of wavelength dependent interferograms during the second time interval. A processor preconditions the first and second sets of wavelength dependent interferograms; multiples the first preconditioned set of wavelength dependent interferograms and the second preconditioned set of wavelength dependent interferograms; and computes a first two-dimensional spatial domain image composed of a set of A-scans derived from the first set of wavelength dependent interferograms, a second two-dimensional spatial domain image composed of a set of A-scans derived from the second set of wavelength dependent interferograms, a spatial offset between the first and second spatial domain images, and a combined spatial domain image formed from the first and second spatial domain images.

In further embodiments, the processor may be configured to compute a shift between each corresponding A-scan pair from a multiplicative product of the corresponding A-scans derived respectively from the preconditioned first and second sets of wavelength dependent interferograms; and compute the spatial offset between the first and second spatial domain images using the mean, median or mode of the shifts between the set of individual A-scan pairs corresponding to the two sets of wavelength dependent interferograms.

In still further embodiments, the processor may be further configured to precondition the first and second sets of wavelength dependent interferograms using one or more of wavelength to wavenumber resampling; background and/or reference subtraction; and addition of a wavelength dependent phase function.

In some embodiments, the processor may be configured to compute combined spatial domain images using addition of the first and second spatial domain images; using a depth-dependent blending of the first and second spatial domain images; and/or using an adaptive combination of the first and second spatial domain images.

Further embodiments of the present inventive concept provide methods of increasing useful image depth of a Fourier domain optical coherence tomography (FDOCT) system. The methods include setting a first reference optical path length along a reference path of an FDOCT imaging system to be shorter than an optical path length to a proximal-most surface of a region of interest of a subject; acquiring a first set of wavelength dependent interferograms with the first reference optical path length; setting a second reference optical path length along a reference path of a FDOCT imaging system to be longer than an optical path length to a distal-most surface of the region of interest of the subject; acquiring a second set of wavelength dependent interferograms with the second reference optical path length; multiplying one or more preconditioned wavelength dependent interferograms from the first set of wavelength dependent interferograms by one or more preconditioned wavelength dependent interferograms from the second set of wavelength dependent interferograms; computing a spatial domain image for each of the two sets of wavelength dependent interferograms; deriving a spatial offset between the spatial domain images derived from the two sets of wavelength dependent interferograms; and combining the computed spatial domain images to create a third spatial domain image.

In still further embodiments of the present inventive concept, the spatial offset between the first and second spatial domain images may be computed using the mean, median or mode of shifts of the individual A-scan pairs within each respective spatial domain image. The method may further include computing a shift of each A-scan pair using the multiplicative product of the preconditioned first and second wavelength dependent interferograms.

In some embodiments, preconditioning of wavelength dependent interferograms may include wavelength to wavenumber resampling; background and/or reference subtraction; and/or addition of a wavelength dependent phase function.

In further embodiments, the combined spatial domain images may be computed from addition of the first and second spatial domain images; a depth-dependent blending of the first and second spatial domain images and/or an adaptive combination of the first and second spatial domain images.

DETAILED DESCRIPTION OF EMBODIMENTS

Figure 1:
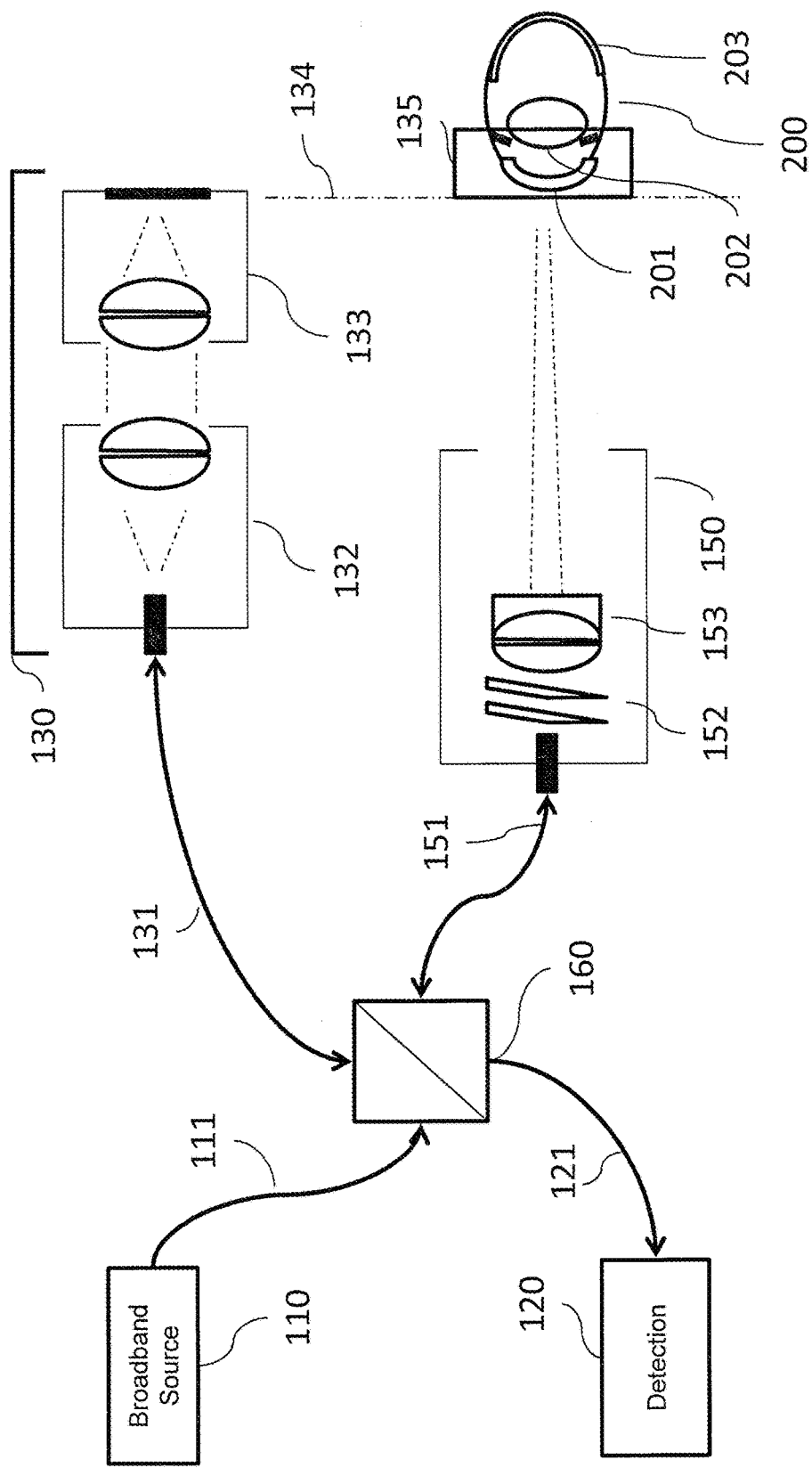
FIG. 1 is an example optical coherence tomography (OCT) system used in accordance with some embodiments of the present inventive concept.

The present inventive concept will be described more fully hereinafter with reference to the accompanying figures, in which embodiments of the inventive concept are shown. This inventive concept may, however, be embodied in many alternate forms and should not be construed as limited to the embodiments set forth herein.

Accordingly, while the inventive concept is susceptible to various modifications and alternative forms, specific embodiments thereof are shown by way of example in the drawings and will herein be described in detail. It should be understood, however, that there is no intent to limit the inventive concept to the particular forms disclosed, but on the contrary, the inventive concept is to cover all modifications, equivalents, and alternatives falling within the spirit and scope of the inventive concept as defined by the claims. Like numbers refer to like elements throughout the description of the figures.

The terminology used herein is for the purpose of describing particular embodiments only and is not intended to be limiting of the inventive concept. As used herein, the singular forms "a", "an" and "the" are intended to include the plural forms as well, unless the context clearly indicates otherwise. It will be further understood that the terms "comprises", "comprising," "includes" and/or "including" when used in this specification, specify the presence of stated features, integers, steps, operations, elements, and/or components, but do not preclude the presence or addition of one or more other features, integers, steps, operations, elements, components, and/or groups thereof. Moreover, when an element is referred to as being "responsive" or "connected" to another element, it can be directly responsive or connected to the other element, or intervening elements may be present. In contrast, when an element is referred to as being "directly responsive" or "directly connected" to another element, there are no intervening elements present. As used herein the term "and/or" includes any and all combinations of one or more of the associated listed items and may be abbreviated as "/".

Unless otherwise defined, all terms (including technical and scientific terms) used herein have the same meaning as commonly understood by one of ordinary skill in the art to which this inventive concept belongs. It will be further understood that terms used herein should be interpreted as having a meaning that is consistent with their meaning in the context of this specification and the relevant art and will not be interpreted in an idealized or overly formal sense unless expressly so defined herein.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element without departing from the teachings of the disclosure. Although some of the diagrams include arrows on communication paths to show a primary direction of communication, it is to be understood that communication may occur in the opposite direction to the depicted arrows.

As optical coherence tomography (OCT) is based on low-coherence interferometry, images acquired with OCT necessarily suffer from signal-degrading speckle. This speckle lowers perceived image quality, signal to noise ratio (SNR) and resolution. Although speckle is deterministic, and therefore not random noise, speckle patterns are sensitive to the optical path length traversed by the incident and returning field. Therefore, an effective means of reducing signal-degrading speckle in OCT is image compounding, where images acquired at slightly different spatial positions (or incidence angles) are summed. If the speckle patterns are fully decorrelated between the two images, the image SNR improves by the square root of is the number of images summed together. If these images are acquired sequentially, which is generally simpler to achieve than simultaneous acquisitions, the images must be registered to correct for patient motion prior to being summed. For applications where real-time display of the OCT data is required, for example, intrasurgical OCT, a fast and accurate registration algorithm is generally required to enable display of registered and averaged OCT images at video rate.

An OCT system appropriate to the inclusion of the inventive technology is discussed in commonly assigned U.S. patent application Ser. No. 13/836,576, the disclosure of which is hereby incorporated herein by reference as if set forth in its entirety. The example system discussed therein, illustrated in FIG. 1, illustrates an FDOCT engine including a broadband source 110, a reference arm 130 and a sample arm 150 coupled to each other by a beamsplitter 160. The beamsplitter 160 may be, for example, a fiber optic coupler or a bulk or micro-optic coupler. The beamsplitter 160 may provide from about a 50/50 to about a 90/10 split ratio. In some embodiments, the beamsplitter 160 may include a beam combiner. However, the beam combiner (not shown) may also be a separate element of the system of FIG. 1 without departing from the scope of the present inventive concept.

As further illustrated in FIG. 1, the beamsplitter 160 is also coupled to a wavelength or frequency sampled detection module 120 over a detection path 121 that may be provided by an optical fiber.

As further illustrated in FIG. 1, the source 110 is coupled to the beamsplitter 160 by a source path 111. The source 111 may be, for example, a continuous wave broadband superluminescent diode, a pulsed broadband source, or tunable source. The reference arm 130 is coupled to the beamsplitter 160 over a reference arm path 131. Similarly, the sample arm 150 is coupled to the beamsplitter 160 over the sample arm path 151. The source path 111, the reference arm path 131 and the sample arm path 151 may all be provided by optical fiber or a combination of optical fiber, free-space, and bulk- or micro-optical elements.

The reference arm of the FDOCT retinal imaging system may include a collimator assembly 132, a variable attenuator 181 and a mirror assembly 133, and a path length matching position 134, i.e. optical path length matching between the reference arm path length and the sample arm path length to the subject region of interest. As further illustrated, the sample arm 150 may include a dual-axis scanner assembly 152 and an objective lens with variable focus 153. The sample illustrated in FIG. 1 is an eye 200 including a cornea 201, ocular lens 202 and retina 203. A representation of an FDOCT imaging window 135 is illustrated near the cornea 201. It will be understood that the system of FIG. 1 is provided for example only and, therefore, embodiments of the present inventive concept should not be limited to this configuration.

Figure 2A:
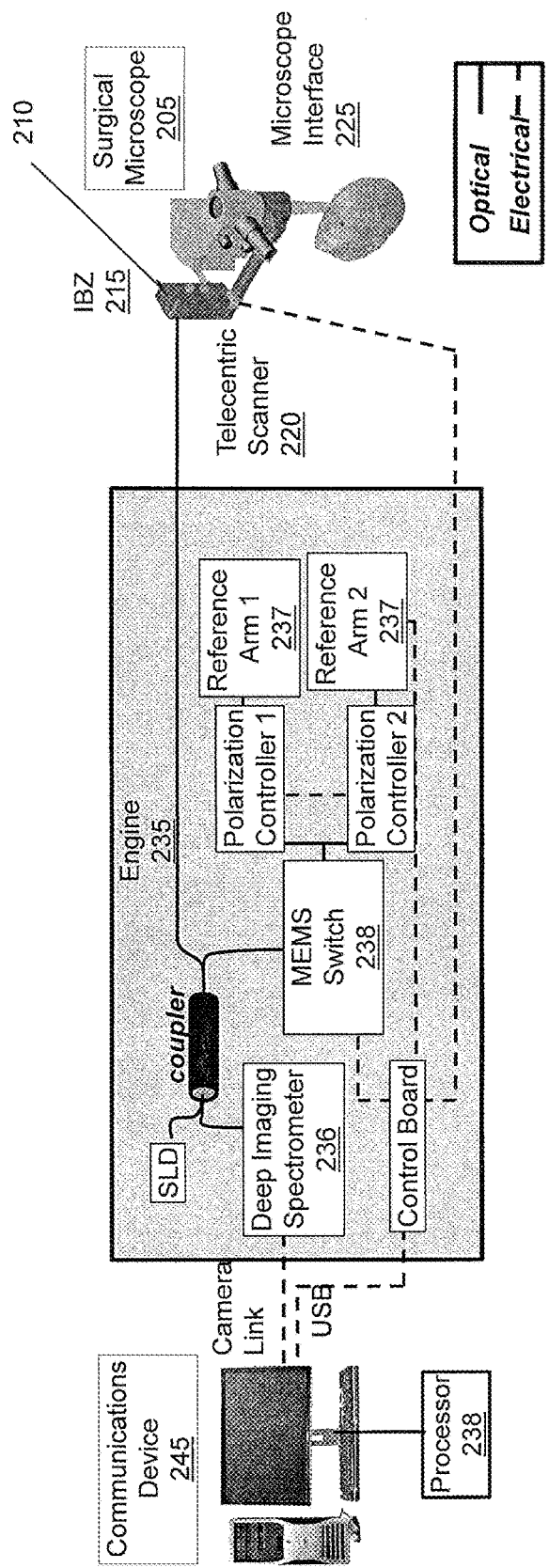
FIG. 2A is a block diagram illustrating a more detailed system including the OCT engine, microscope and computer interface in accordance with some embodiments of the present inventive concept.

Referring now to FIG. 2A, a more detailed block diagram illustrating a system including the OCT engine, surgical microscope and the computer interface in accordance with some embodiments of the present inventive concept. Embodiments illustrated in FIG. 2A may be appropriate for cornea, refractive and cataract surgery where extended imaging depth may be desirable. As illustrated in FIG. 2A, the system 200 includes a surgical microscope 205, an OCT engine 235 and a communications device 245. Solid lines in FIG. 2A depict optical connections and dotted lines in FIG. 2A depict electrical connections. However, it will be understood that embodiments of the present inventive concept are not limited the configuration illustrated in FIG. 2A.

As illustrated in FIG. 2A, the Scan Head 210 includes an Input Beam Zoom (IBZ) 215, a telecentric scanner 220 and a microscope interface 225. The IBZ 215 module provides control of the OCT beam's focal depth and numerical aperture (NA). The telecentric scanner 220 has a wide field-of-view and highly telecentric scan optics optimized for both anterior and posterior imaging. The microscope interface 225 provides interchangeable microscope-specific interface modules to integrate the OCT system to the microscope.

As further illustrated in FIG. 2A, the FDCOT engine 235 includes a spectrometer 236, dual reference arms 237 and a microelectromechanical systems (MEMS) switch 238. The spectrometer 236 may be a Bioptigen 4300 or 4400 "Deep Imaging" spectrometer, which provides an 8 mm or 16 mm imaging range, respectively, with a 4 µm or 8 µm pixel resolution, at up to 140 kHz line-rate. The dual reference arms 237 include dual, motorized reference arms with automated control of reference delay, power and polarization. The MEMS switch is configured to rapidly toggle between each reference arm between successive frame acquisitions.

In addition to the hardware of the OCT engine 235 and the surgical microscope 205, the system 200 of FIG. 2A also provides various software and user interface capabilities. For example, in combination with the communications device 245, the system may provide a streamlined user interface, supporting both "real-time" and "stop-and-scan" imaging modes; imaging presets that automatically optimize imaging parameters for specific surgical procedures; automated optimization of imaging parameters through image analysis feedback algorithms; enhanced depth imaging, an imaging mode that uses dual reference arm technology to reduce sensitivity fall-off and extend the OCT imaging range up to 14 mm; and advanced image analysis tools to aid in surgical decision making. As illustrated in FIG. 2A, the communications device may include a processor 238, details of which will be discussed further below with respect to FIGS. 13-14.

Figure 2B:
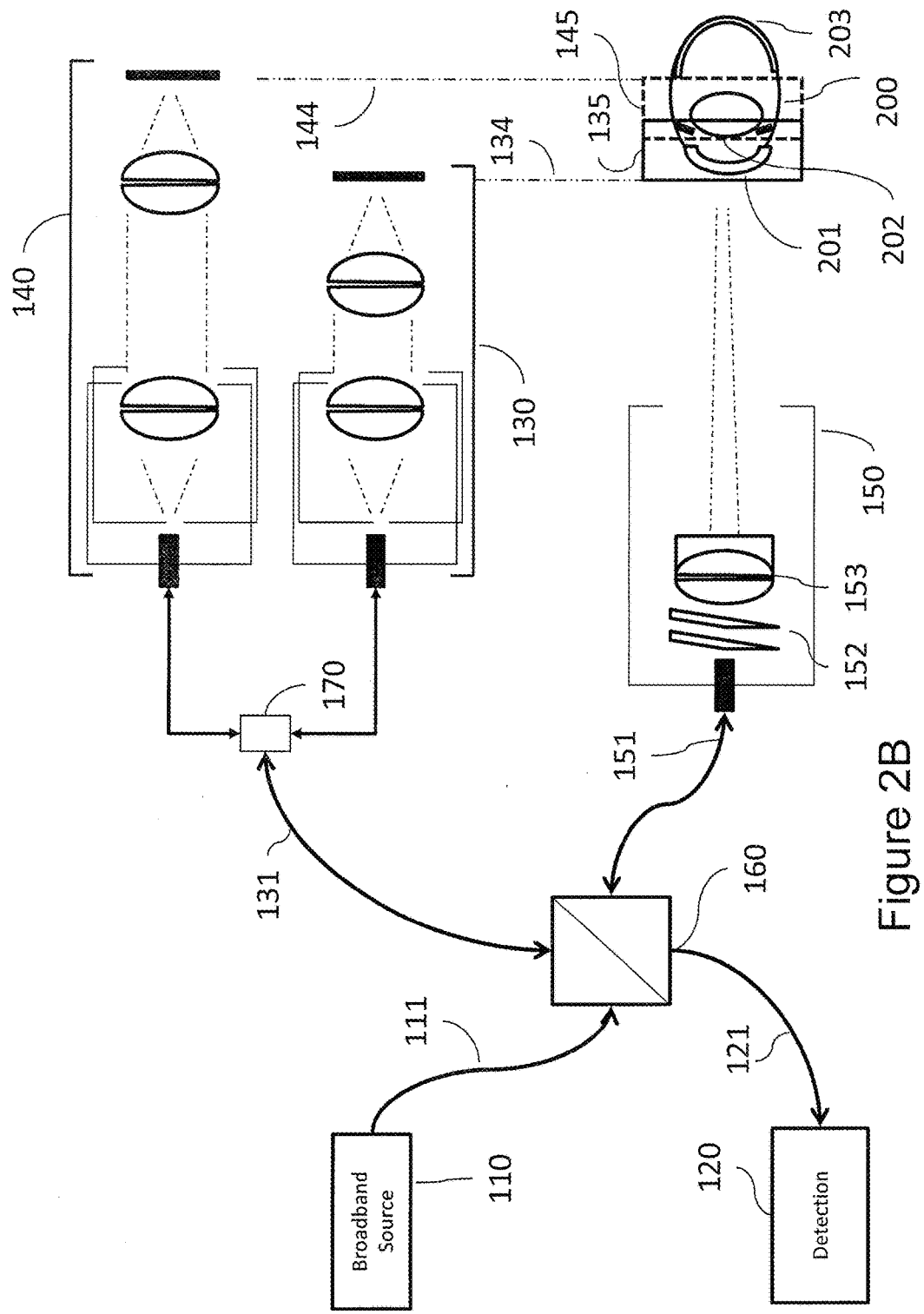
FIG. 2B is a block diagram illustrating relationships between reference arm positions and structures of the eye in accordance with some embodiments of the present inventive concept.

Referring now to FIG. 2B, components of the system of FIG. 2A will not be discussed. FIG. 2B illustrates an FDOCT engine including a broadband source 110, a reference arm 130 and a sample arm 150 coupled to each other by a beamsplitter/combiner 160. The beamsplitter/combiner 160 may be, for example, a fiber optic coupler or a bulk or micro-optic coupler. The beamsplitter/combiner 160 may provide from about a 50/50 to about a 90/10 split ratio.

As further illustrated in FIG. 2B, the beamsplitter/combiner 160 is also coupled to a wavelength or frequency sampled detection module 120 over a detection path 121 that may be provided by an optical fiber. The source 110 is coupled to the beamsplitter/combiner 160 by a source path 111. The source 111 may be, for example, a continuous wave broadband superluminescent diode, a pulsed broadband source, or tunable source. The reference arm 130 is coupled to the beamsplitter/combiner 160 over a reference arm path 131. Similarly, the sample arm 150 is coupled to the beamsplitter/combiner 160 over the sample arm path 151. The source path 111, the reference arm path 131 and the sample arm path 151 may all be provided by optical fiber or a combination of optical fiber, free-space, and bulk- or micro-optical elements.

The system of FIG. 2B comprises 2 reference arms 130, 140 of similar construction and different optical path length matching positions 134, 144, i.e. optical path length matching between the reference arm path lengths and the sample arm path length to the subject region of interest. As further illustrated, the sample arm 150 may include a dual-axis scanner assembly 152 and an objective lens with variable focus 153. The sample illustrated in FIG. 2B is an eye 200 including a cornea 201, ocular lens 202 and retina 203. A representation of an FDOCT imaging window 135, 145 for each reference position is illustrated near the cornea 201. It will be understood that the system of FIG. 2B is provided for example only and, therefore, embodiments of the present inventive concept should not be limited to this configuration.

Input Beam Zoom Module

Figure 3A:
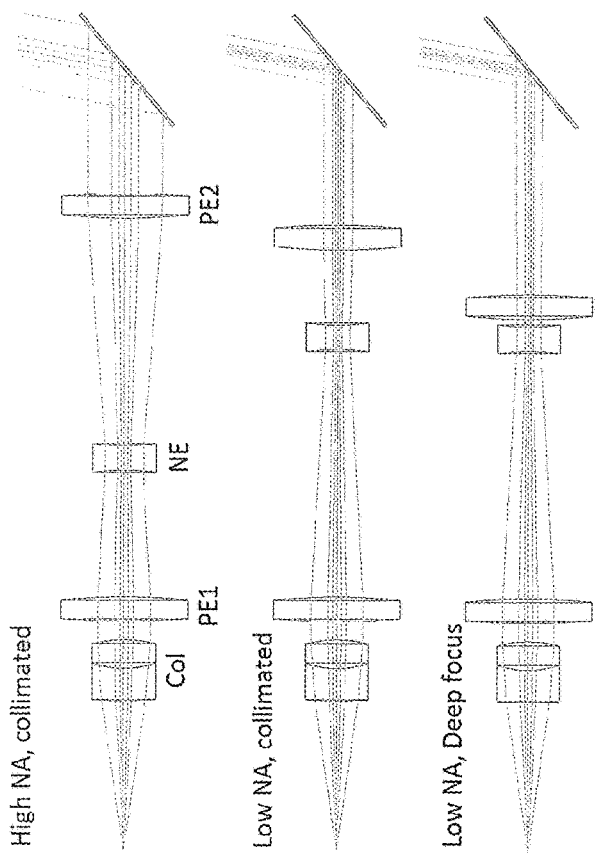
FIG. 3A is a block diagram illustrating an example input beam zoom (IBZ) in accordance with some embodiments of the present inventive concept.

Referring now to FIG. 3A, an IBZ module 215 (FIG. 2A) in accordance with some embodiments of the present inventive concept will be discussed. As illustrated in FIG. 3A, the IBZ includes a collimating lens (Col) followed by three lens groups: a stationary positive element (PE1), a translating (movable) negative element (NE), and a translating (movable) positive element (PE2). By translating (moving) the two non-stationary groups (NE and PE2) to calibrated positions, the focal depth and NA of the output beam can be adjusted. By inserting this IBZ module into the OCT sample arm prior to the scanning mirrors, the focal depth and NA of the OCT beam can be adjusted and optimized for a particular procedure or application. In some embodiments, the two translating (movable) lens groups (NE and PE2) are actuated by miniature stepper motors providing rapid and repeatable adjustment of the beam parameters. In some embodiments, the design also includes two control knobs mounted on a control board (FIG. 2A) which will allow the user to scroll through pre-calibrated focal length and NA settings, allowing the surgeon to adjust imaging parameters without having to interface with the software.

In particular, as the movable lens groups are moved from one position to the next, the distance between the lens groups determines the beam parameters. For example, the top diagram in FIG. 3A illustrates the position of the lens groups for a collimated beam with high NA. Similarly, the middle diagram of FIG. 3A illustrates the position of the lens groups for a collimated beam with low NA. Finally, the bottom diagram in FIG. 3A illustrates the position of the lens groups for deep focus beam with low NA.

Figure 3B:
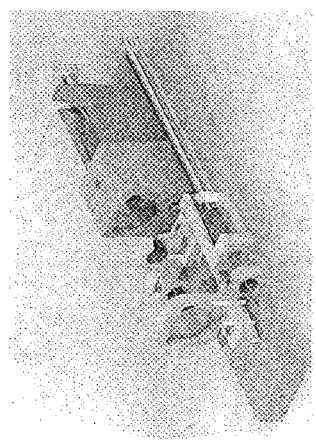
FIG. 3B is a diagram illustrating a three dimensional rendering of a complete IBZ module including mechanical assemblies and motors in accordance with some embodiments of the present inventive concept.

FIG. 3B is a diagram illustrating a three dimensional rendering of a complete IBZ module including mechanical assemblies and motors in accordance with some embodiments of the present inventive concept.

Wide Field-of-View Telecentric Scan Optics

Figure 4A:
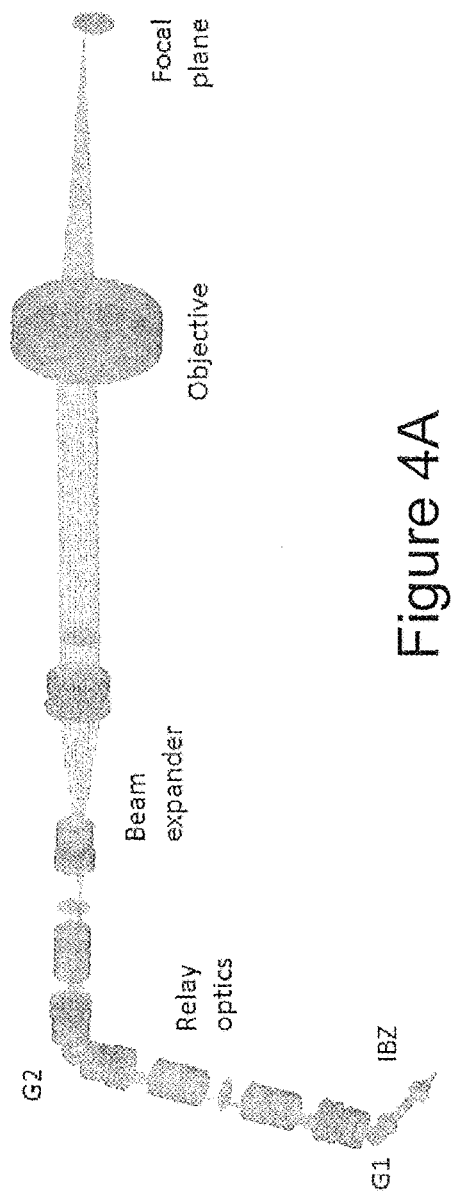
FIG. 4A is a diagram illustrating optics in accordance with some embodiments of the present inventive concept.

As illustrated in FIG. 4A, downstream of the IBZ module, the system includes a sophisticated optical scanner that produces a high quality telecentric scan. In particular, downstream of the IBZ, scanning mirrors G1 and G1 are shown in combination with relay optics. A dichroic mirror is not shown, but may be included. The optics G1/G2 are provided between the IBZ and a beam expander before and objective lens, which leads to a focal plane. The optical scanner illustrated in FIG. 4A provides excellent resolution and telecentricity, achieving diffraction limited performance and better than 2 μm of optical path length difference (OPLD) over a 25 mm field-of-view (FOV) for anterior segment imaging. This performance is maintained throughout the entire range of addressable focal lengths and beam NAs from the IBZ module 215. Depending on the beam NA, spot sizes range from 9 μm to 30 μm (FWHM) and depth-of-focus ranges from 0.6 mm to 6.3 mm. This system will increase the likelihood that high quality OCT images are acquired regardless of imaging parameters. The high degree of telecentricity of the scan also increases the likelihood that quantitative analysis, for example, corneal aberrometry, can be performed with minimal correction or calibration. For posterior segment imaging, the FOV and lateral resolution will depend on both the patient optics and the fundus viewing lens employed. Nevertheless, the wide FOV and diffraction-limited performance for anterior segment imaging translate exceptionally well to retinal imaging. The FOV for retinal imaging is nominally 75 degrees with a 60 diopter fundus viewing lens and 45 degrees with a 40 diopter lens.

Figure 4B:
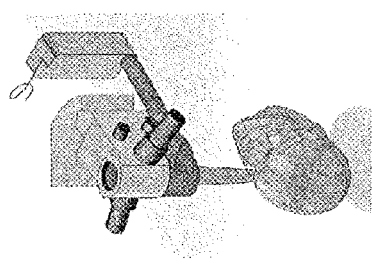
FIG. 4B is an illustration of the optics of FIG. 4A integrated with a microscope.

FIG. 4B is an illustrating depicting the system of FIG. 4A in a microscope.

Interchangeable Microscope Interface Module

In some embodiments of the present inventive concept, to facilitate integration with a variety of surgical microscopes, interchangeable microscope-specific interface modules may be used. These modules contain the dichroic beamsplitter through which the OCT beam is introduced, as well as microscope-specific mounting hardware to integrate into the infinity space of the surgical microscope. Surgical microscopes in accordance with some embodiments of the present inventive concept include an "infinity space." This is a space above the final objective lens before the stereo beams converge. In some embodiments, the dichroic is inserted into this "infinity space." This space with one or more spectrally diverse or polarization diverse filters may be used to couple additional accessories to the surgical microscope system. Accessories may include, but are not limited to, for example, a video camera, wavefront analysis system, an auto refractor, a scanning laser ophthalmoscope and/or a laser. In some cases the coupling element will be within the infinity space, but in some cases a coupling element may exist elsewhere in the OCT signal path.

To reduce the axial length of the interface module, the dichroic beamsplitter is oriented at 38 degrees and, thus, introduces less than 45 mm of additional optical path into the infinity space of the surgical microscope. This design reduces the increase in distance from the surgeon to the patient, and also increases the likelihood that the microscope view is not altered by the presence of the OCT system.

Deep Imaging Spectrometers

Figures 5A, 5B:
FIG. 5A is a B-scan illustrating an anterior segment spatial domain image obtained in accordance with some embodiments of the present inventive concept.
FIG. 5B is a B-scan acquired with the same parameters used to acquire the image in FIG. 5A, but having a cropped depth range to highlight axial resolution in accordance with some embodiments of the present inventive concept.

Referring now to FIGS. 5A and 5B, Bioptigen's R4300 and R4400 spectrometer provide excellent imaging range and imaging speed without sacrificing image quality or resolution, making them the ideal spectrometer for both anterior and posterior segment imaging. In particular, FIG. 5A illustrates a representative B-scan acquired using an R4300 spectrometer of an anterior segment image, single frame, 1000 A-scans×2048 depth pixels, 50 μs integration time. Similarly, FIG. 5B illustrates a representative B-scan of the retinal image acquired with same parameters as in FIG. 5A, but having the depth range cropped to highlight axial resolution. As illustrated, using Bioptigen's wavenumber-linearization technology, discussed in commonly assigned U.S. patent application Ser. No. 13/428,247, incorporated by reference above, these spectrometers boast 8 mm and 16 mm of imaging range respectively, excellent fall-off performance (−11 dB at 80% zmax), axial pixel resolutions of 4 μm and 8 μm and linerates of up to 140 kHz. Despite the increased imaging speed, the high optical efficiency of the spectrometer (>85% optical efficiency) increased the likelihood that sensitivity is not adversely affected, with systems achieving >100 dB sensitivity at 70 kHz.

Surgery-Specific Acquisition Software

Figure 6:
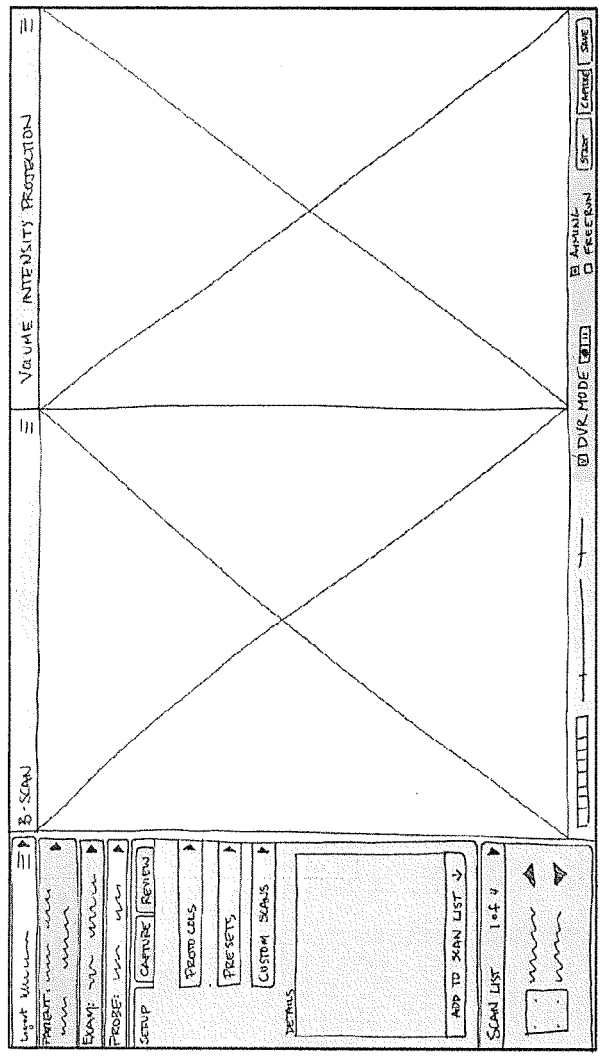
FIG. 6 is a diagram illustrating a conceptual sketch of a surgery-specific software user interface in accordance with some embodiments of the present inventive concept.

A surgery-specific version of Bioptigen's acquisition software, InVivoVue, features several changes to facilitate surgical imaging. Referring to FIG. 6, a diagram illustrating a conceptual sketch of a surgery-specific software user interface in accordance with some embodiments of the present inventive concept will be discussed. In particular, FIG. 6 illustrates a streamlined user interface, which enables rapid selection and toggling of imaging presets and feedback controls. Surgical presets and other controls are accessible via the left panel, with the majority of the screen space devoted to the OCT and volume intensity projection (VIP) images. In some embodiments, Bioptigen's existing foot pedal controls are retained, facilitating hands-free control of the OCT system. The software features both "real-time" and "stop-and-scan" imaging modes, each tuned to make most efficient use of the OCT system. In "real-time" mode, the integration time and reference power can be automatically adjusted to match the B-scan acquisition rate to video rate (30 fps), providing the highest possible SNR for the live image display. In "stop-and-scan" mode, acquisition runs at a user-defined imaging speed (up to 140 kHz) with the B-scan display updated at video rate. Additional data from the scan is immediately available via a "detailed review" mode. In both modes, the software provides a live fundus image derived from the VIP.

Procedure-Specific Imaging Presets and Workflows

The OCT engine in accordance with some embodiments of the present inventive concept may include Bioptigen's newly developed motorized reference arms and polarization controllers, which enable automated control of the reference delay, power and polarization. Combined with the traditional scan controls and additional controls conferred by the IBZ, these technologies enable fast, repeatable and automatic control of virtually all OCT imaging parameters. These include reference delay, reference power, reference polarization, focal depth, NA, integration time, numerical dispersion compensation parameters, scan shape, scan length and scan density. By calibrating these parameters appropriately prior to surgery, presets can be defined for various surgical procedures. In some embodiments, software modules provide programmable surgical workflows, wherein a series of imaging presets can be programmed to occur in series. Presets and workflows can then be recalled during surgery via buttons on the user interface or through the foot pedal. This reduces initial set-up time and also allows maneuver-specific and procedure-specific imaging conditions to be rapidly toggled.

Automatic Image Optimization Through Image Analysis Feedback Algorithm

In addition to imaging presets, the software modules may also be configured to provide algorithms to adjust imaging parameters in real-time to maintain imaging performance during surgery. For example, in response to axial patient or microscope motion, the reference arm and focal depth settings automatically track to keep the image sharp and centered in the imaging range, using image analysis algorithms to provide real-time feedback. Control algorithms allow the camera integration time to be dynamically adjusted. By increasing integration time (and simultaneously reducing reference power), the OCT system sensitivity can be dramatically increased, by as much as 18 dB, at the expense of imaging speed. This enables images to be acquired from patients whose posterior segments could otherwise not be imaged with OCT due to cataracts or cloudy media attenuating the OCT beam.

Extended Depth Imaging

Figure 7:
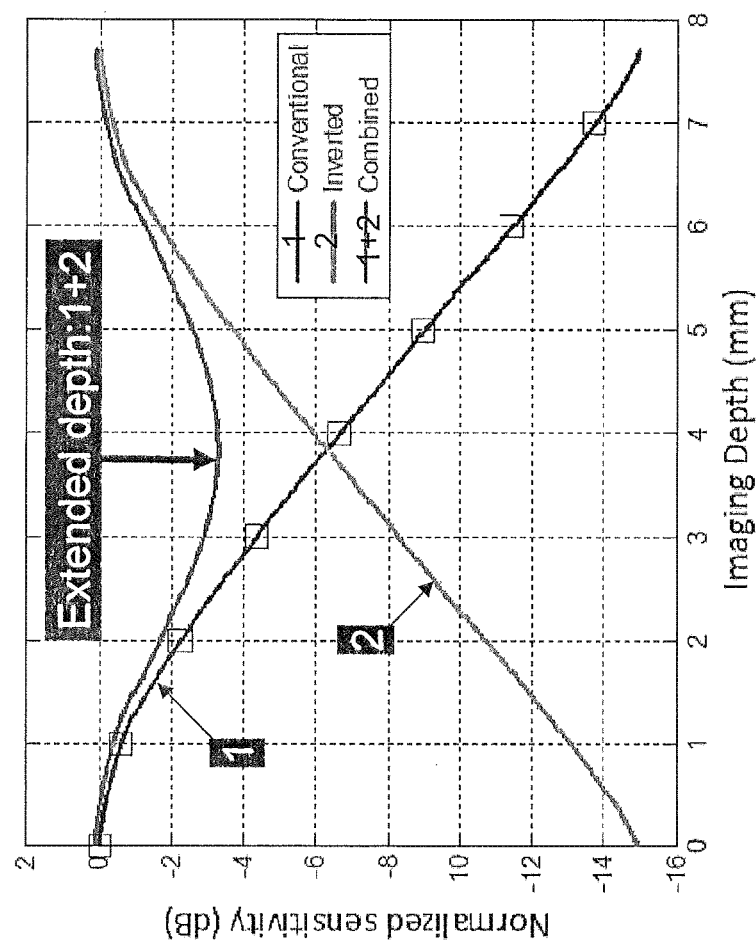
FIG. 7 is a graph illustrating measured sensitivity falloff data from an R4300 spectrometer in conventional mode (1) and projected sensitivities for inverted (2) and extended depth (1+2) modes in accordance with some embodiments of the present inventive concept.

The OCT engine in accordance with some embodiments of the present inventive concept includes two motorized reference arms, selectable by a fast (<1 ms) MEMS optical switch as illustrated in FIG. 2A. This switch operates sufficiently fast to toggle in less time than is required for the scanning mirrors to retrace between B-scans and, thus, enables switching between B-scans. By offsetting the two reference arms by the Fourier domain imaging range, $z_{max}$, and acquiring two scans at the same position using each reference arm, the two images can be combined to produce an image with nearly uniform sensitivity over the entire imaging range. By increasing the separation between the two reference arms further, the imaging range can be further increased at the expense of sensitivity, up to approximately 14 mm or 28 mm for the R4300 and R4400 spectrometers, respectively. FIG. 7 is a graph illustrating measured sensitivity falloff data from an R4300 spectrometer in conventional mode (1) and projected sensitivities for inverted (2) and extended depth (1+2) modes in accordance with some embodiments of the present inventive concept. Leveraging the superior fall-off performance of Bioptigen's "Deep Imaging" spectrometers, which experience a sensitivity drop of only −6 dB at one-half $z_{max}$, the maximum sensitivity variance of a combined frame would be only −3 dB, delivering essentially uniform imaging sensitivity over the entire imagine range as illustrated in the graph of FIG. 7. When extending the imaging range even further, for example to 14 mm or 28 mm for the R4300 and R4400 respectively, the maximum sensitivity drop over the combined frame would be approximately −9 dB.

Advanced Image Analysis Tools

In order to take full advantage of the vast amount of information collected by the intraoperative OCT system, embodiments of the present inventive concept provide automated image analysis tools. Findings from early adopters of Bioptigen's perioperative imaging solutions have identified a number of applications where image analysis and image segmentation can aid in surgical decision making. For example, complete removal of residual LECs and good capsule-IOL adhesion are correlated with lower incidence of posterior capsule opacification.

Figures 8A, 8B:
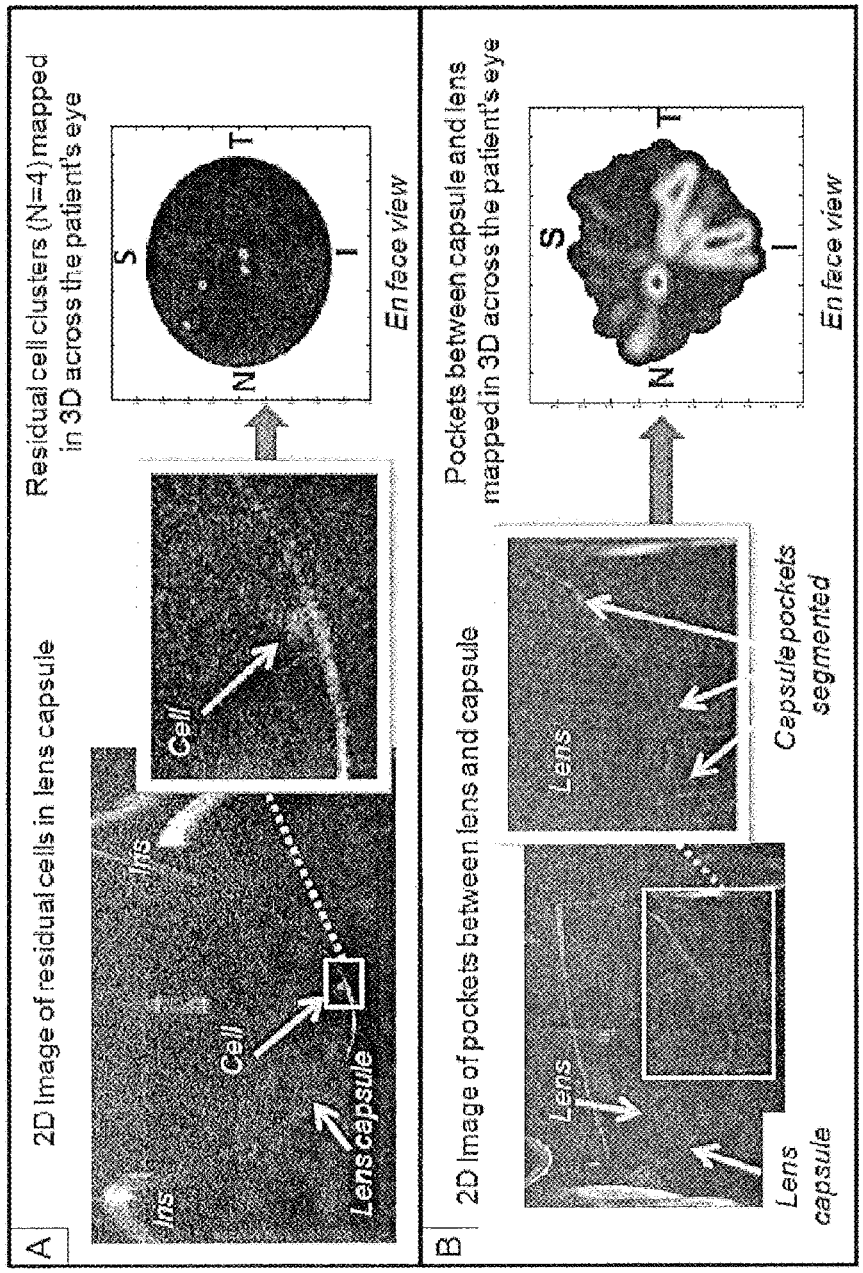
FIG. 8A is diagram illustrating a B-scan of a posterior lens capsule showing residual LEC, inset showing individual cell, and en face map of residual LECs in accordance with some embodiments of the present inventive concept.
FIG. 8B is a diagram illustrating a B-scan showing IOL in posterior capsule (yellow arrows point to areas of poor adhesion), inset showing capsule pockets, and en face distance map showing LECs in accordance with some embodiments of the present inventive concept.

FIG. 8A is diagram illustrating a B-scan of a posterior lens capsule showing residual LEC, inset showing individual cell, and en face map of residual LECs in accordance with some embodiments of the present inventive concept. FIG. 8A illustrates the automated segmentation of LECs can enable surgeons to verify that these cells have been completely removed.

FIG. 8B is a diagram illustrating a B-scan showing IOL in posterior capsule (yellow arrows point to areas of poor adhesion), inset showing capsule pockets, and en face distance map showing LECs in accordance with some embodiments of the present inventive concept. FIG. 8B illustrates that segmentation algorithms can also be developed to assess adhesion of the lens capsule to the IOL. In the posterior eye, segmentation algorithms can be used to identify persistent membranes following an ILM or ERM peel.

Axial Registration

In certain applications, especially ophthalmic imaging where the patient fixates on a target, axial motion dominates over lateral motion. In these applications, lateral motion between rapidly acquired frames (typically separated by 50 ms or less) can be ignored, and only axial motion needs to be corrected. In these cases, registration of the OCT images can be constrained to a single dimensional problem. This problem can be quickly solved using a modified form of phase correlation registration by taking advantage of the form of the OCT data. Traditional phase correlation registration techniques exploit the fact that a translation in the space domain corresponds to a phase shift in the Fourier domain to quickly compute the translation between two images without requiring computationally expensive cross-correlation. For two-dimensional (2D) rigid registration, the traditional algorithm functions as follows referring to FIG. 9:

1) The 2D fast Fourier transform (FFT) of one image (block 933) is multiplied, element-wise, by the complex conjugate of the 2D FFT of the second image (blocks 943/944);
2) The product matrix is normalized, element-wise, by its element-wise absolute value (block 953);
3) The magnitude of the 2D inverse-FFT of the normalized matrix is computed; and
4) The coordinates of the peak of the magnitude matrix correspond to the shift between the two images (974/975), in pixels (block 963).

Figure 9:
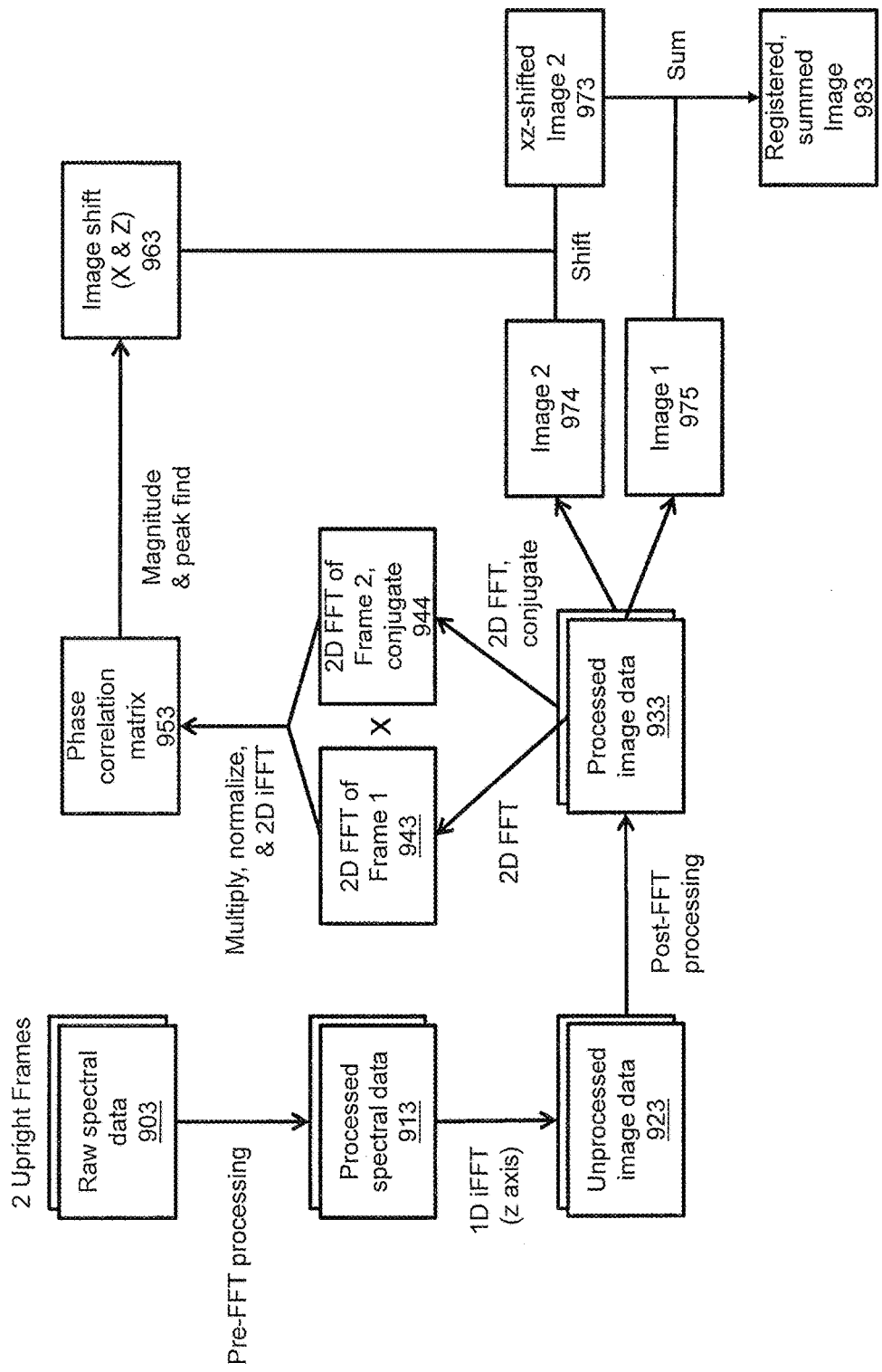
FIG. 9 is a flowchart illustrating steps for integrating the 2D rigid registration algorithm into an OCT processing pipeline in accordance with some embodiments of the present inventive concept.

Referring now to FIG. 9, steps for integrating the 2D rigid registration algorithm into an OCT processing pipeline will be discussed. In embodiments of FIG. 9, the operations begin with the raw spectral data 903 corresponding to two upright frames and produces a registered, summed frame 983 from image 1 975 the shifted image 2 973. In some embodiments, the Pre-FFT (FIG. 9) processing stage may consist of spectral resampling, DC subtraction and other signal preconditioning steps. The post-FFT preconditioning (FIG. 9) may consist of log compression, contrast adjustment and noise suppression.

This technique can be sped up substantially by taking advantage of three aspects of this problem:

1) The OCT data is acquired directly in the Fourier domain (i.e. an (inverse) FFT has already been implicitly performed in the axial direction);
2) Only axial registration of the images is required; and
3) In cases where two inverted frames are being combined, the spectral data corresponding to the two frames are already complex conjugates of each other.

As a result of these three facts, we can directly multiply the preconditioned spectral frames 913 (i.e. after resampling and dispersion-compensation, but before FFT) of the two images and take the one dimensional (1D) FFT (in the axial dimension) of the result to provide the unprocessed image data 923. In other words, rather than performing three computationally expensive 2D FFTs on an N×M matrix discussed above, we need only perform M 1D FFT's on N-element vectors. Thus, the computational complexity is reduced from 3 NMlog(NM) to NMlog(N). For typical OCT volumes consisting of between 1024 and 4096 spectral samples and between 500 and 2000 lines, this represents a reduction in computation complexity by a factor of between ~5.2× and ~6.6×.

In cases where the two images are not inverted (i.e., both frames are upright), the complex conjugate of one frame must be computed prior to this step. Note that for systems that do not apply numerical dispersion compensation, the preconditioned spectral frame has no imaginary component, and thus the complex conjugates are identical.

Summing the resulting frame across the lateral dimension yields a line, the peak of which is the axial shift between the two images. It will be understood that the FFT of the processed spectral frame is the full range image (i.e., both positive and negative frequencies). This results in an offset of N/2 in the shift that is computed.

Figure 10:
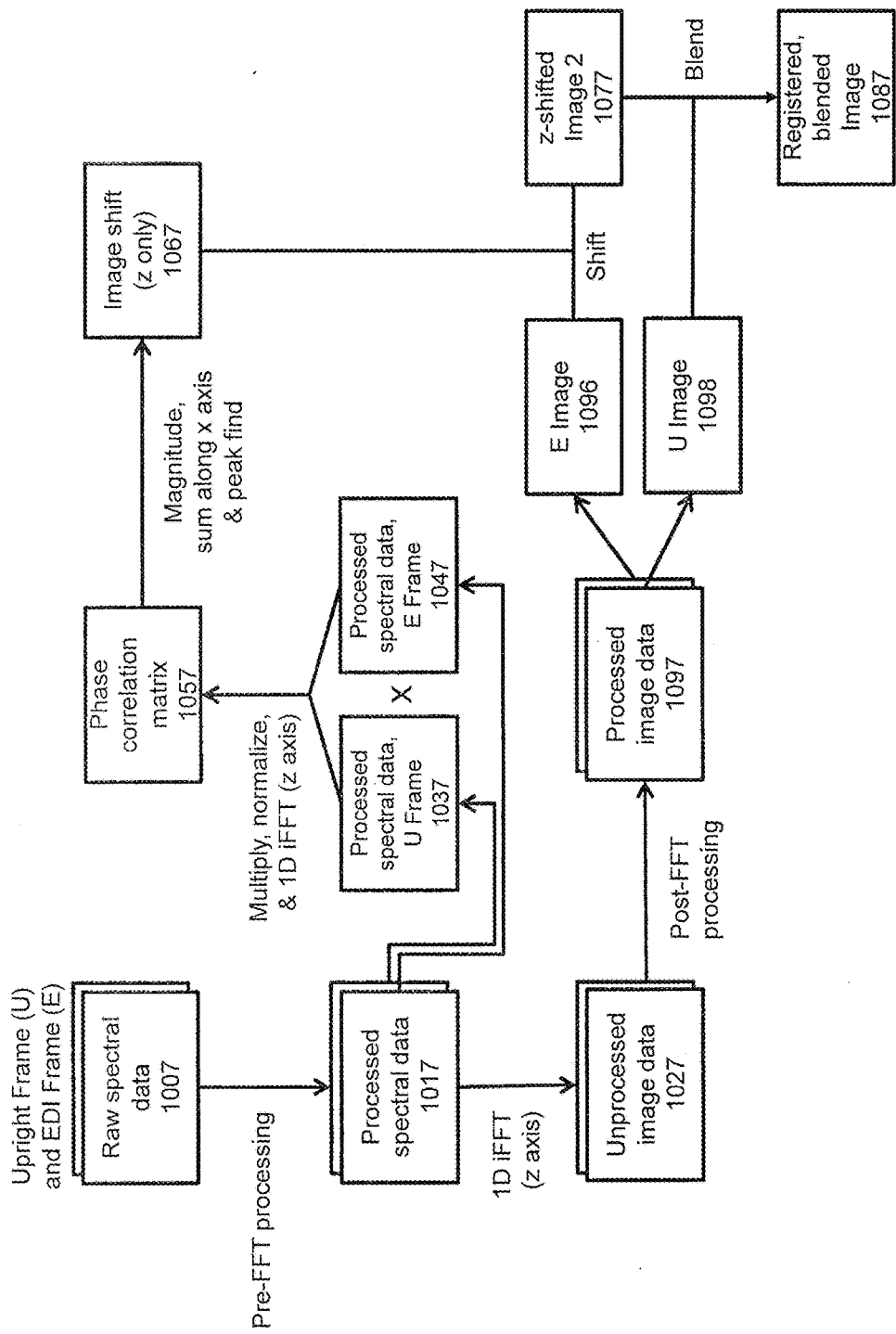
FIG. 10 is a flowchart illustrating steps for integrating the 2D rigid registration algorithm into an OCT processing pipeline in accordance with some embodiments of the present inventive concept.

FIG. 10 is a flowchart illustrating steps for integrating the 2D rigid registration algorithm into an OCT processing pipeline in accordance with some embodiments of the present inventive concept. In embodiments illustrated in FIG. 10, the algorithm begins with an upright frame and an EDI (inverted) frame 1007 and produces a registered, blended frame 1087. Registration in this case is only performed in the z-dimension. Blending algorithms may consist of naïve summation of the two images (U image 1098 and z-shifted image 2 1077), or may be more sophisticated, as described below.

Lateral Registration

In situations where the assumption that lateral motion can be ignored does not hold, the algorithm can be extended to include lateral registration. Because all of the mathematical operations performed in this modified algorithm (after the computation of the complex conjugate, where necessary) are linear functions, including the FFT, the second dimension of the standard phase correlation algorithm can be inserted before collapsing the problem to one dimension. In this case, prior to multiplying the two processed spectral frames together (blocks 1037/1047), a 1D FFT should be applied in the lateral dimension (blocks 1017-1027). (blocks 1007, 1017 and 1027 correspond to pre-FFT preconditioning) The resulting two matrices should then be multiplied element-wise, and the co-ordinates of the peak of the resulting matrix correspond to the axial and lateral shift (blocks 1057, 1067).

Because axial and lateral registration are separable, and because all of the functions applied are linear, lateral registration can instead be performed as a single dimensional problem on the processed image data (block 1097). The processed image data 1097 is separated into E image 1096 and U image 1098 before being blended to provide the registered blended image 1087. This method is actually faster than methods discussed above with respect to FIG. 9, as the initial axial registration algorithm is necessarily applied to both the real and complex conjugate images. After axial registration, the complex conjugate images can be discarded, resulting in images with only half the original number of axial pixels. Furthermore, as OCT images often contain many blank horizontal lines with little structure, a simple thresholding algorithm can be used to restrict the image to an axial region of interest. As a result of these two simplifications, the resulting image has substantially fewer depth lines, and thus the phase correlation computation requires substantially fewer FFTs. As the most computationally expensive step in phase correlation registration is the FFT, the combination of these two simplifications reduces the computation cost of the lateral registration step by a factor of 10 or more. After restricting the region of interest of the image, lateral registration can be performed using the 1D phase correlation algorithm.

Figure 11:
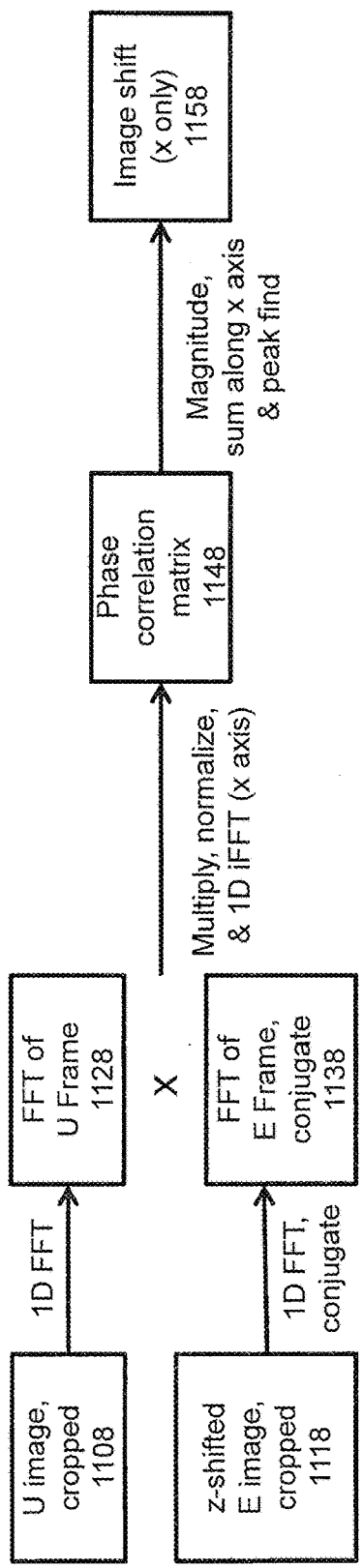
FIG. 11 is a flowchart illustrating steps for determining a lateral shift beginning with upright (U) 1108 and EDI (E) 1118 images that have been cropped to the region of interest in accordance with some embodiments of the present inventive concept.

Referring now to the flowchart of FIG. 11, beginning with upright (U) 1108 and EDI (E) 1118 images that have been cropped to the region of interest. The resulting lateral shift 1158 that is computed must then be applied to the EDI image (1128, 1138, 1148) prior to blending 1158. In particular, as illustrated in FIG. 11, a 1D FFT is performed on a cropped U image 1108 to provide and FFT of the U frame 1128. Similarly, a 1D FFT (conjugate) is performed on an FFT of an E frame, conjugate 1138. The FFT of the U frame 1128 and the FFT of the E frame 1138 are multiplied (multiply, normalize and 1D iFFT (x-axis) to provide a phase correlation matrix 1148. The magnitude of the sum along the x-axis and peak find provide the image shift in the x direction 1158.

Image Blending

For systems using multiple reference arms, image blending, rather than straightforward image addition, may improve image quality. This is especially true for systems that acquire images with inverted orientations. This is because OCT image SNR and axial resolution typically degrade with increasing depth.

In image blending, a weighted average is used when combining the two frames to optimize image brightness and resolution. While sophisticated blending approaches have been developed for image mosaicing applications, (e.g. Gaussian feathering/blending), OCT images already have an inherent brightness reduction with depth due to sensitivity falloff. As a result, blending OCT images with a linear blending algorithm yields excellent results.

Figure 12:
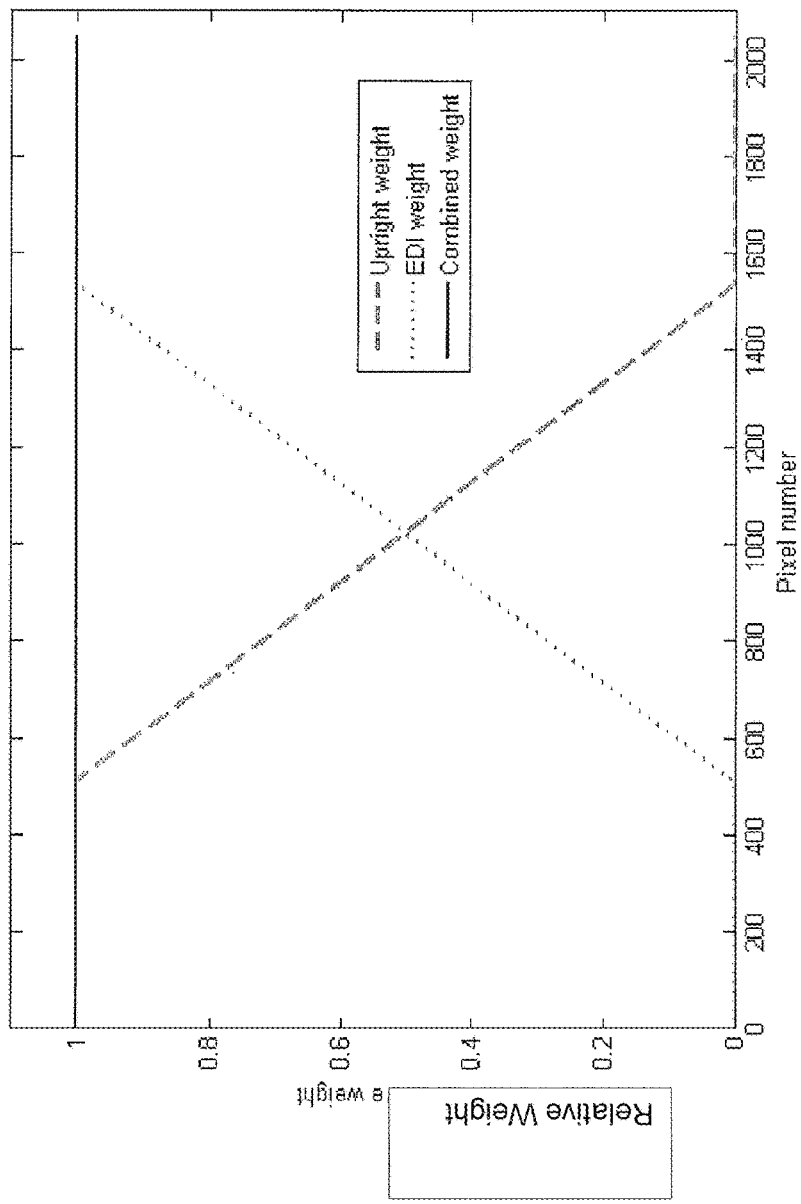
FIG. 12 is a graph of relative weight vs. pixel number in accordance with some embodiments of the present inventive concept.

Referring now to FIG. 12, a graph depicting weights that would be applied to upright and EDI images using one such linear blending algorithm will be discussed. This algorithm functions as follows:

1) A "blend region" coefficient is chosen by the user or through optimization. This is the region over which the image is blended. For example, if the image had 2048 depth pixels and the blend region coefficient was 0.5, the blend region would span 513 to 1536.

2) Image pixels shallower than the blend region (in our example, pixels 1 to 512) are be copied directly from the upright image only into the blended image. Likewise, image pixels deeper than the blend region (1537 to 2048 in the example) are copied directly from the inverted image into the blended image.

3) In the blended region, the two images should be added together, with linearly increasing/decreasing weighting coefficients that always sum to unity.

Because of the very large speed increase associated with the image registration methodologies in the present invention, it becomes possible to register, compound and average images in approximate real-time to increase a depth range or improve signal to noise in high speed optical coherence tomography imaging applications.

As discussed above, some aspects of the present inventive concept may be implemented by a data processing system. Exemplary embodiments of a data processing system 1330 configured in accordance with embodiments of the present inventive concept will be discussed with respect to FIG. 13. As will be understood, the data processing system may be included in a communications device 245 in accordance with some embodiments of the present inventive concept. It may also be included in the engine or be a separate component without departing from the scope of the present inventive concept. The data processing system 1330 may include a user interface 1344, including, for example, input device(s) such as a keyboard or keypad, a display, a speaker and/or microphone, and a memory 1336 that communicate with a processor 1338. The data processing system 1330 may further include I/O data port(s) 1346 that also communicates with the processor 1338. The I/O data ports 1346 can be used to transfer information between the data processing system 1330 and another computer system or a network using, for example, an Internet Protocol (IP) connection. These components may be conventional components such as those used in many conventional data processing systems, which may be configured to operate as described herein.

Figure 13:
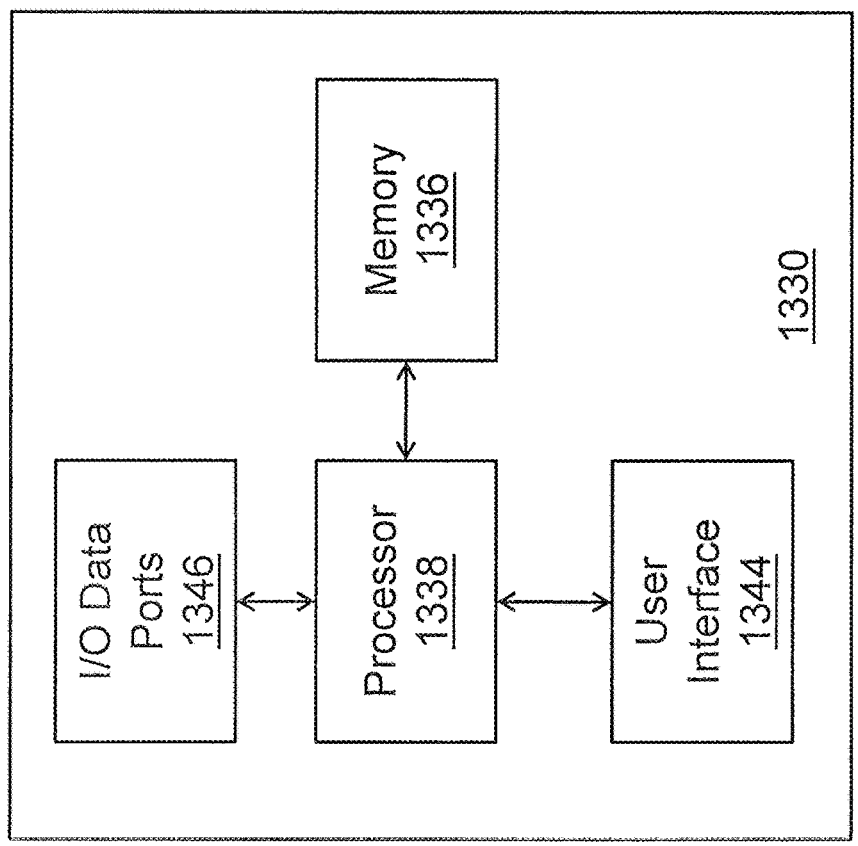
FIG. 13 is block diagram illustrating a data processing system configured in accordance with embodiments of the present inventive concept.
Figure 14:
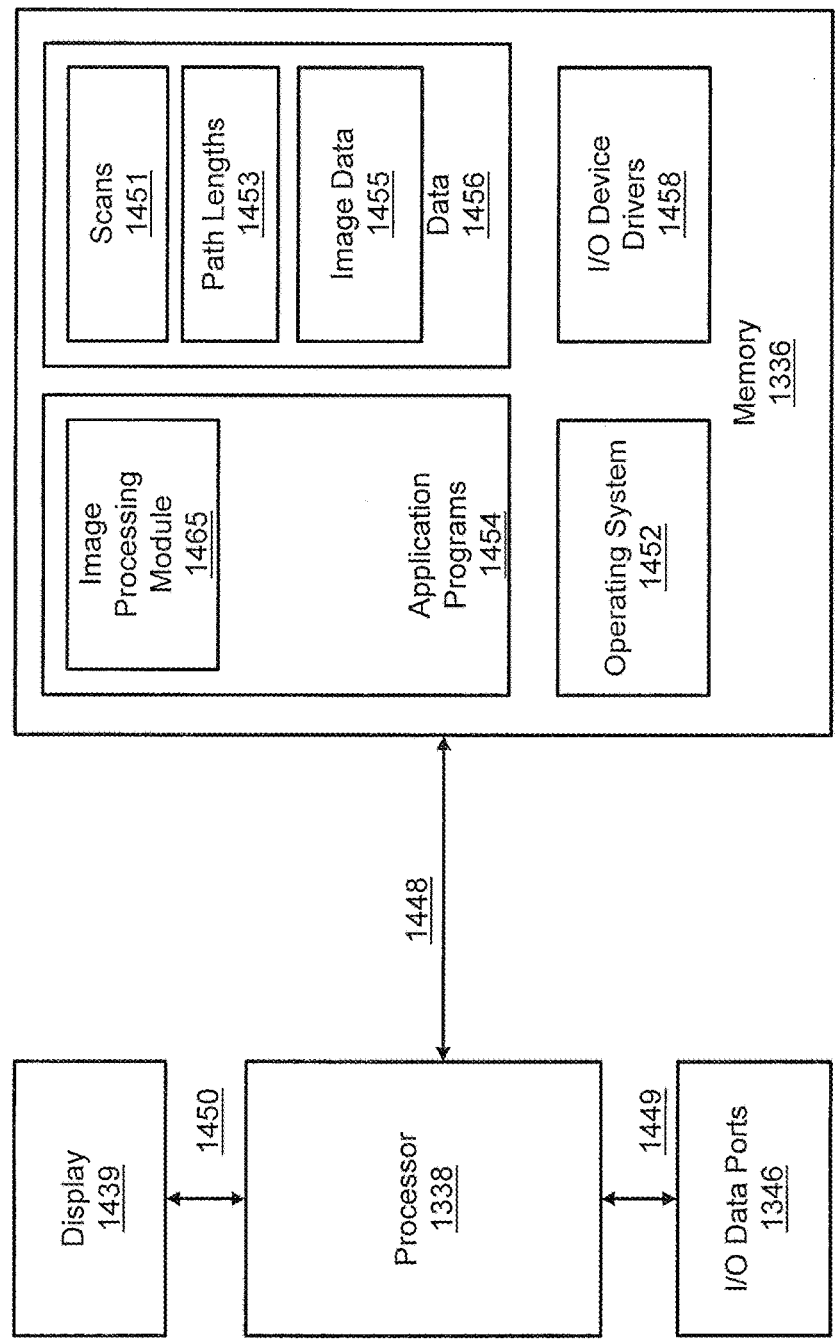
FIG. 14 is a more detailed block diagram of a data processing system of FIG. 13 in accordance with some embodiments of the present inventive concept.

Referring now to FIG. 14, a more detailed block diagram of a data processing system of FIG. 13 is provided that illustrates systems, methods, and computer program products in accordance with some embodiments of the present inventive concept, which will now be discussed. As illustrated in FIG. 14, the processor 1338 communicates with the memory 1336 via an address/data bus 1448, the I/O data ports 1346 via address/data bus 1449 and the electronic display 1439 via address/data bus 1450. The processor 1338 can be any commercially available or custom enterprise, application, personal, pervasive and/or embedded microprocessor, microcontroller, digital signal processor or the like. The memory 1336 may include any memory device containing the software and data used to implement the functionality of the data processing system 1330. The memory 1336 can include, but is not limited to, the following types of devices: ROM, PROM, EPROM, EEPROM, flash memory, SRAM, and DRAM.

As further illustrated in FIG. 14, the memory 1336 may include several categories of software and data used in the system: an operating system 1452; application programs 1454; input/output (I/O) device drivers 1458; and data 1456. As will be appreciated by those of skill in the art, the operating system 1452 may be any operating system suitable for use with a data processing system, such as OS/2, AIX or zOS from International Business Machines Corporation, Armonk, N.Y., Windows95, Windows98, Windows2000 or WindowsXP, or Windows CE or Windows 7 from Microsoft Corporation, Redmond, Wash., Palm OS, Symbian OS, Cisco IOS, VxWorks, Unix or Linux. The I/O device drivers 1458 typically include software routines assessed through the operating system 1452 by the application programs 1454 to communicate with devices such as the I/O data port(s) 1346 and certain memory 1336 components. The application programs 1454 are illustrative of the programs that implement the various features of the some embodiments of the present inventive concept and may include at least one application that supports operations according to embodiments of the present inventive concept. Finally, as illustrated, the data 1456 may include the scans 1451, path length data 1453 and general image data 1455 and any of the data acquired and stored by the system, which may represent the static and dynamic data used by the application programs 1454, the operating system 1452, the I/O device drivers 1458, and other software programs that may reside in the memory 1336.

As further illustrated in FIG. 14, according to some embodiments of the present inventive concept, the application programs 1454 include an image processing module 1465. While the present inventive concept is illustrated with reference to image processing module 1465 being an application program in FIG. 14, as will be appreciated by those of skill in the art, other configurations fall within the scope of the present inventive concept. For example, rather than being an application program 1454, these circuits and modules may also be incorporated into the operating system 1452 or other such logical division of the data processing system. Furthermore, while the image processing module 1465 is illustrated in a single system, as will be appreciated by those of skill in the art, such functionality may be distributed across one or more systems. Thus, the present inventive concept should not be construed as limited to the configuration illustrated in FIG. 14, but may be provided by other arrangements and/or divisions of functions between data processing systems. For example, although FIG. 14 is illustrated as having various circuits, one or more of these circuits may be combined without departing from the scope of the present inventive concept.

It will be understood that the image processing module 1465 may be used to implement various portions of the present inventive concept capable of being performed by a data processing system. For example, the image processing module 1465 may be used to process and assess the images produced by the OCT system according to some embodiments of the present inventive concept.

An example of operations will now be discussed with respect to FIGS. 1, 2 and 14. The system includes a source 110 of broadband optical radiation. The beamsplitter 160 is coupled to the source and divides the source radiation into a reference path 131 and a sample path 151. As illustrated in FIG. 2A, the reference path may include an optical switch 238 to switch the reference path between a first path 237 having a first reference reflection at a first reference optical path length and a second path 237 having a second reference reflection at a second reference optical path length. A beam combiner may be include in the beamsplitter 160 or may be provided as a separate element. The beam combiner mixes source radiation reflected from a subject in the sample path with source radiation returned from the first reference reflection during a first time interval and the second reference reflection during a second time interval. The detection system 120 detects a first wavelength dependent interferogram during the first time interval and a second wavelength dependent interferogram during the second time interval. The processor 238/1338 preconditions the first and second wavelength dependent interferograms; multiples the first preconditioned wavelength dependent interferogram and the second preconditioned wavelength dependent interferogram during a third time interval following the second time interval; and computes a first A-scan from the first wavelength dependent interferogram; a second A-scan from the second wavelength dependent interferogram; a spatial offset between the first and second A-scans derived from the multiplicative product of the preconditioned first and second wavelength dependent interferograms; and a combined A-scan from the first and second A-scans.

It will be understood that all the various scans, path lengths and intermediate calculations may be stored in the data 1456, specifically, scans 1451, path lengths 1453 and image data 1455 and may be processed by the processor 238/1338.

The processor 238/1338 is further configured to precondition the first and second spectral interferograms using one or more of wavelength to wavenumber resampling; background and/or reference subtraction; and addition of a wavelength dependent phase function. The processor may compute the combined A-scans using addition of the first and second A-scans; using a depth-dependent blending of the first and second A-scans; and/or using an adaptive combination of the first and second A-scans without departing from the scope of the present inventive concept.

As discussed above, the system of FIGS. 1 and 2 may be, for example, an FDOCT. The FDOCT system may be an SDOCT or a SSOCT system without departing from the scope of the present inventive concept.

In some embodiments of the present inventive concept, the detection system may be a spectrometer and the broadband source of optical radiation may radiate a time varying optical spectrum.

In some embodiments of the present inventive concept, the detection system 120 detects a first set of wavelength dependent interferograms during the first time interval and a second set of wavelength dependent interferograms during the second time interval. The processor may be further configured to precondition the first and second sets of wavelength dependent interferograms; multiply the first preconditioned set of wavelength dependent interferograms and the second preconditioned set of wavelength dependent interferograms; and compute a first two-dimensional spatial domain image composed of a set of A-scans derived from the first set of wavelength dependent interferograms, a second two-dimensional spatial domain image composed of a set of A-scans derived from the second set of wavelength dependent interferograms, a spatial offset between the first and second spatial domain images, and a combined spatial domain image formed from the first and second spatial domain images.

Figure 15:
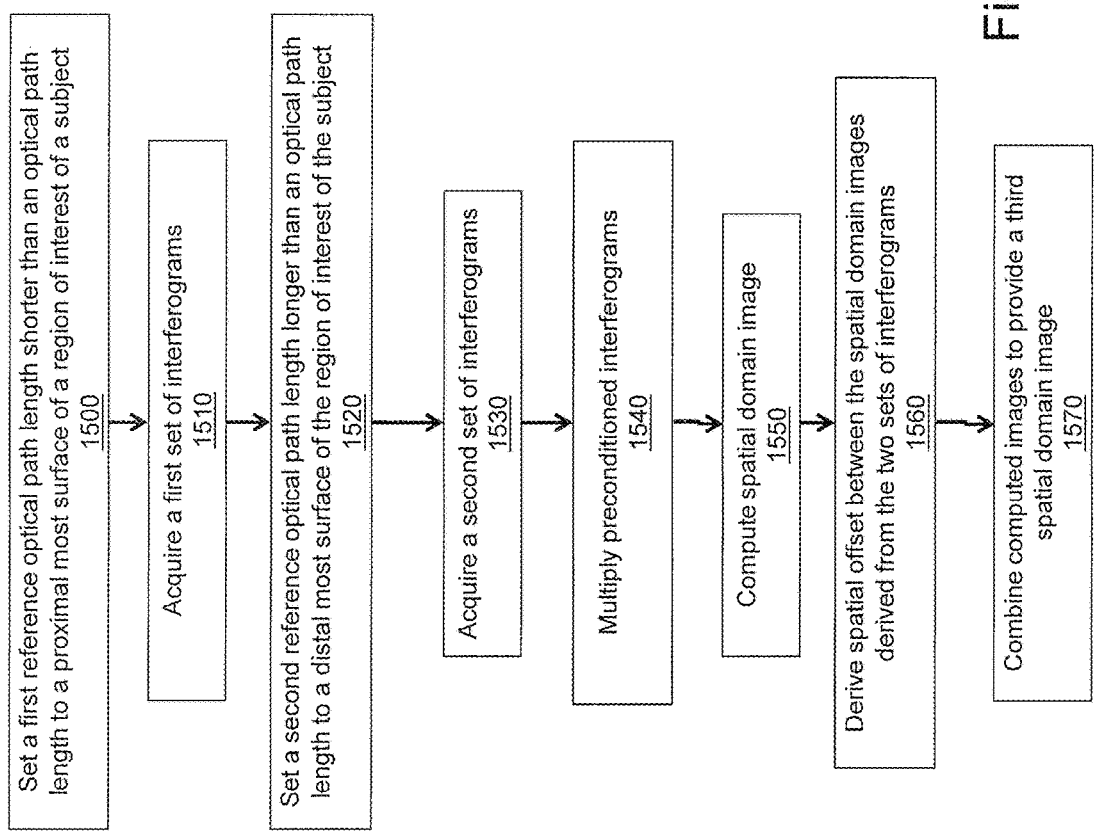
FIG. 15 is a flowchart illustrating operations of an OCT system in accordance with some embodiments of the present inventive concept.

Referring now to the flowchart of FIG. 15, operations for increasing useful image depth of a Fourier domain optical coherence tomography (FDOCT) system in accordance with some embodiments of the present inventive concept will be discussed. As illustrated in FIG. 15, operations begin at block 1500 by setting a first reference optical path length along a reference path of an FDOCT imaging system to be shorter than an optical path length to a proximal-most surface of a region of interest of a subject. A first set of wavelength dependent interferograms with the first reference optical path length is acquired (block 1510). A second reference optical path length is set along a reference path of a FDOCT imaging system to be longer than an optical path length to a distal-most surface of the region of interest of the subject (block 1520). A second set of wavelength dependent interferograms with the second reference optical path length is acquired (block 1530). One or more preconditioned wavelength dependent interferograms from the first set of wavelength dependent interferograms is multiplied by one or more preconditioned wavelength dependent interferograms from the second set of wavelength dependent interferograms (block 1540). A spatial domain image is computed for each of the two sets of wavelength dependent interferograms (block 1550). A spatial offset between the spatial domain images derived from the two sets of wavelength dependent interferograms is derived (block 1560). The computed spatial domain images are combined to create a third spatial domain image (block 1570).

In some embodiment, deriving the spatial offset includes computing the spatial offset between the first and second spatial domain images using the mean, median or mode of shifts of the individual A-scan pairs within each respective spatial domain image. Operations may further include computing a shift of each A-scan pair using the multiplicative product of the preconditioned first and second wavelength dependent interferograms.

In some embodiments preconditioning of wavelength dependent interferograms may include wavelength to wavenumber resampling; background and/or reference subtraction; and/or addition of a wavelength dependent phase function.

The combined spatial domain images may be computed from addition of the first and second spatial domain images; a depth-dependent blending of the first and second spatial domain images and/or an adaptive combination of the first and second spatial domain images.

Example embodiments are described above with reference to block diagrams and/or flowchart illustrations of methods, devices, systems and/or computer program products. It is understood that a block of the block diagrams and/or flowchart illustrations, and combinations of blocks in the block diagrams and/or flowchart illustrations, can be implemented by computer program instructions. These computer program instructions may be provided to a processor of a general purpose computer, special purpose computer, and/or other programmable data processing apparatus to produce a machine, such that the instructions, which execute via the processor of the computer and/or other programmable data processing apparatus, create means (functionality) and/or structure for implementing the functions/acts specified in the block diagrams and/or flowchart block or blocks.

These computer program instructions may also be stored in a computer-readable memory that can direct a computer or other programmable data processing apparatus to function in a particular manner, such that the instructions stored in the computer-readable memory produce an article of manufacture including instructions which implement the functions/acts specified in the block diagrams and/or flowchart block or blocks.

The computer program instructions may also be loaded onto a computer or other programmable data processing apparatus to cause a series of operational steps to be performed on the computer or other programmable apparatus to produce a computer-implemented process such that the instructions which execute on the computer or other programmable apparatus provide steps for implementing the functions/acts specified in the block diagrams and/or flowchart block or blocks.

Accordingly, example embodiments may be implemented in hardware and/or in software (including firmware, resident software, micro-code, etc.). Furthermore, example embodiments may take the form of a computer program product on a computer-usable or computer-readable storage medium having computer-usable or computer-readable program code embodied in the medium for use by or in connection with an instruction execution system. In the context of this document, a computer-usable or computer-readable medium may be any medium that can contain, store, communicate, propagate, or transport the program for use by or in connection with the instruction execution system, apparatus, or device.

The computer-usable or computer-readable medium may be, for example but not limited to, an electronic, magnetic, optical, electromagnetic, infrared, or semiconductor system, apparatus, device, or propagation medium. More specific examples (a non-exhaustive list) of the computer-readable medium would include the following: an electrical connection having one or more wires, a portable computer diskette, a random access memory (RAM), a read-only memory (ROM), an erasable programmable read-only memory (EPROM or Flash memory), an optical fiber, and a portable compact disc read-only memory (CD-ROM). Note that the computer-usable or computer-readable medium could even be paper or another suitable medium upon which the program is printed, as the program can be electronically captured, via, for instance, optical scanning of the paper or other medium, then compiled, interpreted, or otherwise processed in a suitable manner, if necessary, and then stored in a computer memory.

Computer program code for carrying out operations of data processing systems discussed herein may be written in a high-level programming language, such as Java, AJAX (Asynchronous JavaScript), C, and/or C++, for development convenience. In addition, computer program code for carrying out operations of example embodiments may also be written in other programming languages, such as, but not limited to, interpreted languages. Some modules or routines may be written in assembly language or even micro-code to enhance performance and/or memory usage. However, embodiments are not limited to a particular programming language. It will be further appreciated that the functionality of any or all of the program modules may also be implemented using discrete hardware components, one or more application specific integrated circuits (ASICs), or a field programmable gate array (FPGA), or a programmed digital signal processor, a programmed logic controller (PLC), or microcontroller.

It should also be noted that in some alternate implementations, the functions/acts noted in the blocks may occur out of the order noted in the flowcharts. For example, two blocks shown in succession may in fact be executed substantially concurrently or the blocks may sometimes be executed in the reverse order, depending upon the functionality/acts involved. Moreover, the functionality of a given block of the flowcharts and/or block diagrams may be separated into multiple blocks and/or the functionality of two or more blocks of the flowcharts and/or block diagrams may be at least partially integrated.

In the drawings and specification, there have been disclosed exemplary embodiments of the inventive concept. However, many variations and modifications can be made to these embodiments without substantially departing from the principles of the present inventive concept. Accordingly, although specific terms are used, they are used in a generic and descriptive sense only and not for purposes of limitation, the scope of the inventive concept being defined by the following claims.

That which is claimed is:

1. An optical coherence tomography (OCT) system comprising:
   a source of broadband optical radiation;
   a beamsplitter coupled to the source and dividing the source radiation into a reference path and a sample path, the reference path comprising an optical switch to switch the reference path between a first path having a first reference reflection at a first reference optical path length and a second path having a second reference reflection at a second reference optical path length, different from the first reference optical path length;
   a beam combiner that mixes source radiation reflected from a subject in the sample path with source radiation returned from the first reference reflection during a first time interval and the second reference reflection during a second time interval;
   a detection system that detects a first wavelength dependent interferogram during the first time interval and a second wavelength dependent interferogram during the second time interval; and
   a processor that preconditions the first and second wavelength dependent interferograms; multiplies the first preconditioned wavelength dependent interferogram and the second preconditioned wavelength dependent interferogram to provide a multiplicative product; and computes a first A-scan from the first wavelength dependent interferogram; a second A-scan from the second wavelength dependent interferogram; a spatial offset between the first and second A-scans derived from the multiplicative product of the preconditioned first and second wavelength dependent interferograms; and a combined A-scan from the first and second A-scans,
   wherein the detection system comprises a spectrometer.

2. The system of claim 1, wherein the processor is further configured to precondition the first and second wavelength dependent interferograms using one or more of:
   wavelength to wavenumber resampling;
   background and/or reference subtraction; and
   addition of a wavelength dependent phase function.

3. The system of claim 1, wherein the processor is further configured to compute the combined A-scan using addition of the first and second A-scans.

4. The system of claim 1, wherein the processor is further configured to compute the combined A-scan using a depth-dependent blending of the first and second A-scans.

5. The system of claim 1, wherein the processor is further configured to compute the combined A-scan using an adaptive combination of the first and second A-scans.

6. The system of claim 1, wherein the OCT system is a Fourier domain OCT (FDOCT) system.

7. The system of claim 6:
wherein the OCT system is a swept source OCT (SSOCT) system; and
wherein the broadband source of optical radiation radiates a time varying optical spectrum.

8. An optical coherence tomography (OCT) system comprising:
a source of broadband optical radiation,
a beamsplitter coupled to the source and dividing the source radiation into a reference path and a sample path, the reference path comprising an optical switch to switch the reference path between a first path having a first reference reflection at a first reference optical path length and a second path having a second reference reflection at a second reference optical path length, different from the first reference optical path length;
a beam combiner that mixes source radiation reflected from a subject in the sample path with source radiation returned from the first reference reflection during a first time interval and the second reference reflection during a second time interval;
a detection system that detects a first set of wavelength dependent interferograms during the first time interval and a second set of wavelength dependent interferograms during the second time interval; and
a processor that preconditions the first and second sets of wavelength dependent interferograms; multiplies the first preconditioned set of wavelength dependent interferograms and the second preconditioned set of wavelength dependent interferograms to provide a multiplicative product; and computes a first two-dimensional spatial domain image composed of a set of A-scans derived from the first set of wavelength dependent interferograms, a second two-dimensional spatial domain image composed of a set of A-scans derived from the second set of wavelength dependent interferograms, a spatial offset between the first and second spatial domain images, and a combined spatial domain image formed from the first and second spatial domain images,
wherein the detection system comprises a spectrometer.

9. The system of claim 8, wherein the processor is configured to:
compute a shift between each corresponding A-scan pair from the multiplicative product of the corresponding A-scans derived respectively from the preconditioned first and second sets of wavelength dependent interferograms; and
compute the spatial offset between the first and second spatial domain images using a mean, median or mode of the shifts between the A-scan pairs corresponding to the two sets of wavelength dependent interferograms.

10. The system of claim 8, wherein the processor is further configured to precondition the first and second sets of wavelength dependent interferograms using one or more of:
wavelength to wavenumber resampling;
background and/or reference subtraction; and
addition of a wavelength dependent phase function.

11. The system of claim 8, wherein the processor is configured to compute combined spatial domain images using addition of the first and second spatial domain images.

12. The system of claim 8, wherein the processor is further configured to compute the combined spatial domain images using a depth-dependent blending of the first and second spatial domain images.

13. The system of claim 8, wherein the processor is configured to compute the combined spatial domain images using an adaptive combination of the first and second spatial domain images.

14. The system of claim 8, wherein the OCT system is a Fourier domain OCT system (FDOCT).

15. The system of claim 14:
wherein the OCT system is a swept source OCT system; and
wherein the broadband source of optical radiation radiates a time varying optical spectrum.

16. A method of increasing useful image depth of a Fourier domain optical coherence tomography (FDOCT) system, the method comprising:
setting a first reference optical path length along a reference path of an FDOCT imaging system to be shorter than an optical path length to a proximal-most surface of a region of interest of a subject;
acquiring a first set of wavelength dependent interferograms with the first reference optical path length;
setting a second reference optical path length along a reference path of a FDOCT imaging system to be longer than an optical path length to a distal-most surface of the region of interest of the subject;
acquiring a second set of wavelength dependent interferograms with the second reference optical path length;
multiplying one or more preconditioned wavelength dependent interferograms from the first set of wavelength dependent interferograms by one or more preconditioned wavelength dependent interferograms from the second set of wavelength dependent interferograms to provide a multiplicative product;
computing a spatial domain image for each of the two sets of wavelength dependent interferograms;
deriving a spatial offset between first and second spatial domain images derived from the two sets of wavelength dependent interferograms; and
combining the computed spatial domain images to create a third spatial domain image,
wherein at least one of the steps of the method are performed by at least one processor; and
wherein preconditioning of wavelength dependent interferograms comprises wavelength to wavenumber resampling; background and/or reference subtraction; and addition of a wavelength dependent phase function.

17. The method of claim 16:
wherein deriving the spatial offset comprises computing the spatial offset between the first and second spatial domain images using a mean, median or mode of shifts of the A-scan pairs within each respective spatial domain image, the method further comprising computing a shift of each A-scan pair using the multiplicative product of the preconditioned first and second wavelength dependent interferograms.

18. The method of claim 16, further comprising computing combined spatial domain images from addition of the first and second spatial domain images.

19. The method of claim 16, further comprising computing combined spatial domain images from a depth-dependent blending of the first and second spatial domain images.

20. The method of claim 16, further comprising computing combined images from an adaptive combination of the first and second spatial domain images.

* * * * *